(12) United States Patent
Gozani et al.

(10) Patent No.: US 10,279,179 B2
(45) Date of Patent: May 7, 2019

(54) TRANSCUTANEOUS ELECTRICAL NERVE STIMULATOR WITH AUTOMATIC DETECTION OF USER SLEEP-WAKE STATE

(71) Applicant: Neurometrix, Inc., Waltham, MA (US)

(72) Inventors: Shai Gozani, Brookline, MA (US); Xuan Kong, Acton, MA (US); Tom Ferree, Waltham, MA (US)

(73) Assignee: Neurometrix, Inc., Waltham, MA (US)

( * ) Notice: Subject to any disclaimer, the term of this patent is extended or adjusted under 35 U.S.C. 154(b) by 322 days.

(21) Appl. No.: 14/253,628

(22) Filed: Apr. 15, 2014

(65) Prior Publication Data

US 2014/0309709 A1 Oct. 16, 2014

Related U.S. Application Data

(63) Continuation-in-part of application No. 14/230,648, filed on Mar. 31, 2014, now Pat. No. 9,474,898.
(Continued)

(51) Int. Cl.
*A61N 1/36* (2006.01)
*A61N 1/08* (2006.01)
(Continued)

(52) U.S. Cl.
CPC ........ *A61N 1/36021* (2013.01); *A61B 5/1118* (2013.01); *A61B 5/4809* (2013.01);
(Continued)

(58) Field of Classification Search
CPC ................................. A61N 1/3602; A61N 1/08
(Continued)

(56) References Cited

U.S. PATENT DOCUMENTS 1,741,962 A 12/1929 Theodoropuios
D263,869 S 4/1982 Surniyasu
(Continued)

FOREIGN PATENT DOCUMENTS

CN 1919139 A 2/2007
CN 101626804 1/2010
(Continued)

OTHER PUBLICATIONS

Bjordal JM et al., Transcutaneous electrical nerve stimulation (TENS) can reduce postoperative analgesic consumption. A meta-analysis with assessment of optimal treatment parameters for post-operative pain, European Journal of Pain, 2003, vol. 7(2): 181-188.
(Continued)

*Primary Examiner* — Nadia A Mahmood
(74) *Attorney, Agent, or Firm* — Pandiscio & Pandiscio

(57) ABSTRACT

Apparatus for transcutaneous electrical nerve stimulation in a user, the apparatus comprising:
 a housing;
 stimulation means for electrically stimulating at least one nerve;
 an electrode releasably mounted to the housing and connectable to the stimulation means for electrical stimulation of the at least one nerve;
 monitoring means for monitoring the user's body orientation and movement;
 analysis means for analyzing said orientation and movement; and
 control means for controlling the output of the stimulation means in response to said analysis of said orientation and movement.

56 Claims, 12 Drawing Sheets

Related U.S. Application Data

(60) Provisional application No. 61/811,864, filed on Apr. 15, 2013.

(51) Int. Cl.
*A61B 5/11* (2006.01)
*A61B 5/00* (2006.01)
*A61N 1/04* (2006.01)

(52) U.S. Cl.
CPC ........ *A61N 1/08* (2013.01); *A61B 2562/0219* (2013.01); *A61N 1/0456* (2013.01); *A61N 2001/083* (2013.01)

(58) Field of Classification Search
USPC ........................................................ 607/47
See application file for complete search history.

(56) References Cited

U.S. PATENT DOCUMENTS

| | | |
|---|---|---|
| 4,503,863 A | 3/1985 | Katims |
| 4,605,010 A | 8/1986 | McEwen |
| 4,738,250 A | 4/1988 | Fulkerson et al. |
| 5,063,929 A | 11/1991 | Bartelt et al. |
| 5,121,747 A | 6/1992 | Andrews |
| 5,169,384 A | 12/1992 | Bosniak et al. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 6,099,488 A | 8/2000 | Hung |
| 6,161,044 A | 12/2000 | Silverstone |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Larnping et al. |
| 6,456,884 B1 | 9/2002 | Kenney |
| 6,662,051 B1 | 12/2003 | Eraker et al. |
| D541,042 S | 4/2007 | Andre et al. |
| D566,383 S | 4/2008 | Harris et al. |
| D592,200 S | 5/2009 | Liu |
| D598,556 S | 8/2009 | Chen |
| D607,198 S | 1/2010 | Andre et al. |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 | 8/2010 | Stahmann et al. |
| D625,829 S | 10/2010 | Arbesrnan et al. |
| D629,115 S | 12/2010 | Robertson |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| D680,735 S | 4/2013 | Itabashi et al. |
| 8,421,642 B1 | 4/2013 | McIntosh et al. |
| D688,707 S | 8/2013 | Vincent et al. |
| D705,428 S | 5/2014 | Cheney et al. |
| D712,045 S | 8/2014 | Thornton |
| 8,825,175 B2 | 9/2014 | King |
| 8,862,238 B2 | 10/2014 | Rahimi et al. |
| D716,963 S | 11/2014 | Yosef et al. |
| 8,948,876 B2 | 2/2015 | Gozani et al. |
| D732,682 S | 6/2015 | Porat |
| 9,168,375 B2 | 10/2015 | Rahimi et al. |
| D744,661 S | 12/2015 | Rizzi |
| D750,263 S | 2/2016 | Shigeno et al. |
| D750,798 S | 3/2016 | Yosef et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| D794,331 S | 8/2017 | Grote |
| 9,731,126 B2 | 8/2017 | Ferree et al. |
| D801,542 S | 10/2017 | Anderson |
| D802,780 S | 11/2017 | Hsu |
| D806,669 S | 1/2018 | Kangasmaa et al. |
| D810,843 S | 2/2018 | Karvandi |
| D811,729 S | 3/2018 | Bysshe |
| D813,407 S | 3/2018 | Chen |
| D813,408 S | 3/2018 | Chen |
| D828,569 S | 9/2018 | Mercuro |
| D829,182 S | 9/2018 | Li |
| D830,565 S | 10/2018 | Xu |
| D831,017 S | 10/2018 | Choe et al. |
| D831,221 S | 10/2018 | 8Rnith |
| D831,335 S | 10/2018 | Crease |
| D832,230 S | 10/2018 | Lee et al. |
| 2002/0010497 A1 | 1/2002 | Merfeld et al. |
| 2003/0023192 A1 | 1/2003 | Foxlin |
| 2003/0035506 A1 | 2/2003 | Tybinkowski et al. |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0017895 A1 | 1/2004 | Suzuki et al. |
| 2004/0122483 A1 | 6/2004 | Nathan et al. |
| 2005/0059903 A1 | 3/2005 | Izumi |
| 2005/0080463 A1 | 4/2005 | Stahmann et al. |
| 2006/0085049 A1 | 4/2006 | Cory et al. |
| 2006/0095088 A1 | 5/2006 | De Ridder |
| 2006/0173507 A1 | 8/2006 | Mrva et al. |
| 2006/0190057 A1 | 8/2006 | Reese |
| 2007/0041507 A1 | 2/2007 | Kendall et al. |
| 2007/0276449 A1 | 11/2007 | Gunter et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0312709 A1 | 12/2008 | Volpe et al. |
| 2009/0030476 A1 | 1/2009 | Hargrove |
| 2009/0131993 A1 | 5/2009 | Rousso et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0128851 A1 | 5/2010 | Bailey et al. |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |

(56) References Cited

U.S. PATENT DOCUMENTS

| | | |
|---|---|---|
| 2011/0066209 A1 | 3/2011 | Bodlaender et al. |
| 2011/0224665 A1 | 9/2011 | Crosby et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2013/0096641 A1 | 4/2013 | Strother |
| 2013/0158627 A1 | 6/2013 | Gozani et al. |
| 2013/0217998 A1 | 8/2013 | Mahfouz et al. |
| 2014/0039450 A1 | 2/2014 | Green et al. |
| 2014/0057232 A1 | 2/2014 | Wetmore et al. |
| 2014/0081353 A1 | 3/2014 | Cook et al. |
| 2014/0107729 A1 | 4/2014 | Sumners et al. |
| 2014/0163444 A1 | 6/2014 | Ingvarsson et al. |
| 2014/0245791 A1 | 9/2014 | Proud et al. |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1* | 10/2014 | Gozani .............. A61N 1/36021 607/46 |
| 2014/0336730 A1 | 11/2014 | Simon et al. |
| 2014/0379045 A1 | 12/2014 | Rahimi et al. |
| 2015/0045853 A1 | 2/2015 | Alataris et al. |
| 2015/0174402 A1 | 6/2015 | Thomas et al. |
| 2015/0321000 A1 | 11/2015 | Rosenbluth et al. |
| 2015/0328467 A1 | 11/2015 | Demers et al. |
| 2015/0335288 A1 | 11/2015 | Toth et al. |
| 2016/0367823 A1 | 12/2016 | Cowan et al. |

FOREIGN PATENT DOCUMENTS

| | | | |
|---|---|---|---|
| CN | 102355847 | 2/2012 | |
| CN | 102740919 | 10/2012 | |
| DE | 10 2010 052710 | 5/2012 | |
| JP | 61-171943 | 10/1986 | |
| JP | 4-347140 | 12/1992 | |
| JP | 9-117453 | 5/1997 | |
| JP | 2000-167067 | 6/2000 | |
| JP | 2005-34402 | 2/2005 | |
| JP | 2005-81068 | 3/2005 | |
| JP | 2006-68300 | 3/2006 | |
| JP | 418546 | 9/2008 | |
| WO | WO 97/42999 | 11/1997 | |
| WO | WO 99/64105 | 12/1999 | |
| WO | WO03051453 A2 * | 12/2001 | ........... A61N 1/0452 |
| WO | WO 2003/051453 | 6/2003 | |
| WO | WO 2004/078132 | 9/2004 | |
| WO | WO 2007/061746 | 5/2007 | |
| WO | WO 2008/079757 | 7/2008 | |
| WO | WO 2008/088985 | 7/2008 | |
| WO | WO 2011/075179 | 6/2011 | |
| WO | WO 2011/137193 | 11/2011 | |
| WO | WO 2012/116407 | 9/2012 | |

OTHER PUBLICATIONS

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentaliy induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cruccu G. et al., EFNS guidelines on neurostimulation therapy for neuropathic pain, European Journal of Neurology, 2007, vol. 14: 952-970.

Davies HTO et al., Diminishing returns or appropriate treatment strategy?—an analysis of short-term outcomes after pain clinic treatment, Pain, 1997, vol. 70: 203-208.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Garrison DW et al., Decreased activity of spontaneous and noxiously evoked dorsal horn cells during transcutaneous electrical nerve stimulation (TENS), Pain, 1994, vol. 58: 309-315.

Jelinek HF et al., Electric pulse frequency and magnitude of perceived sensation during electrocutaneous forearm stimulation, Arch Phys Med Rehabil, 2010, vol. 91: 1372-1382.

Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.

Johnson MI et al., Analgesic effects of different frequencies of transcutaneous electrical nerve stimulation on cold-induced pain in normal subjects, Pain, 1989, vol. 39: 231-236.

Johnson MI et al., Transcutaneous Electrical Nerve Stimulation (TENS) and TENS-like devices: do they provide pain relief?, Pain Reviews, 2001, vol. 8: 7-44.

Johnson MI et al., Transcutaneous electrical nerve stimulation for the management of painful conditions: focus on neuropathic pain, Expert Review of Neurotherapeutics, 2011, vol. 11(5): 735-753.

Kantor G et al., The effects of selected stimulus waveforms on pulse and phase characteristics at sensory and motor thresholds, Physical Therapy, 1994, vol. 74(10): 951-962.

Law PPW et al., Optimal stimulation frequency of transcutaneous electrical nerve stimulation on people with knee osteoarthritis, J Rehabil Med, 2004, vol. 36: 220-225.

Leonard G et al., Deciphering the role of endogenous opioids in high-frequency TENS using low and high doses of naloxone, Pain, 2010, vol. 151: 215-219.

Levy et al., A comparison of two methods for measuring thermal thresholds in diabetic neuropathy, Journal of Neurology, Neurosurgery, and Psychiatry, 1989, vol. 52: 1072-1077.

Melzack R et al., Pain mechanisms: A New Theory, Science, 1965, vol. 150(3699): 971-979.

Pantaleao MA et al., Adjusting pulse amplitude during transcutaneous electrical nerve stimulation (TENS) application produces greater hypoalgesia, The Journal of Pain, 2011, vol. 12(5): 581-590.

Pieber K et al., Electrotherapy for the treatment of painful diabetic peripheral neuropathy: a review, Journal of Rehabilitation Medicine, 2010, vol. 42: 289-295.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Fishbain, David A. et al., Transcutaneous Electrical Nerve Stimulation (TENS) Treatment Outcome in Long-Term Users, The Clinical Journal of Pain, Sep. 1996;12(3):201-214.

(56) References Cited

OTHER PUBLICATIONS

Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008;36(6):639-647.

Food and Drug Administration, Draft Guidance for Industry and Staff: Class II Special Controls Guidance Document: Transcutaneous Electrical Nerve Stimulator for Pain Relief, Apr. 5, 2010.

Johnson, M.I. et al., An in-depth study of long-term users of transcutaneous electrical nerve stimulation (TENS). Implications for clinical use of TENS. Pain. Mar. 1991;44(3):221-229.

Kaczmarek, Kurt A. et al.. Electrotactile and Vibrotactile Displays for Sensory Substitution Systems. IEEE Trans. Biomed. Eng. Jan. 1991;38 (1):1-16.

Keller, Thierry et al., Electrodes for transcutaneous (surface) electrical stimulation. J. Automatic Control, University of Belgrade. 2008;18(2):35-45.

Lykken, D.T., Properties of Electrodes Used in Electrodermal Measurement. J. Comp. Physiol. Psychol. Oct. 1959;52:629-634.

Lykken, D.T., Square-Wave Analysis of Skin Impedance. Psychophysiology. Sep. 1970;7(2):262-275.

Oosterhof, Jan et al., Outcome of transcutaneous electrical nerve stimulation in chronic pain: short-term results of a double-blind, randomised, placebo-controlled trial. J. Headache Pain. Sep. 2006;7(4):196-205.

Oosterhof, Jan et al., The long-term outcome of transcutaneous electrical nerve stimulation in the treatment for patients with chronic pain: a randomized, placebo-controlled trial. Pain Pract. Sep. 2012;12(7):513-522.

Van Boxtel, A., Skin resistance during square-wave electrical pulses of 1 to 10 mA. Med. Biol. Eng. Comput. Nov. 1977;15(6):679-687.

Ancoli-Israel, S. et al., The Role of Actigraphy in the Study of Sleep and Circadian Rhythms, Sleep, 2003, 26(3), p. 342-392.

Cole, R.J. et al., Automatic Sleep/Wake Identification From Wrist Activity, Sleep, 1992, 15(5), p. 461-469.

Desantana, J. M. et al., Effectiveness of Transcutaneous Electrical Nerve Stimulation for Treatment of Hyperalgesia and Pain, Current Rheumatology Reports, 2008, 10(6), p. 492-499.

Gilron, I. et al., Chronobiological Characteristics of Neuropathic Pain: Clinical Predictors of Diurnal Pain Rhythmicity, The Clinical Journal of Pain, 2013.

Hori, T. et al., Skin Potential Activities and Their Regional Differences During Normal Sleep in Humans, The Japanese Journal of Physiology, 1970, vol. 20, p. 657-671.

Koumans, A. J. R. et al., Electrodermal Levels and Fluctuations During Normal Sleep, Psychophysiology, 1968, 5(3), p. 300-306.

Kripke, D.F. et al., Wrist Actigraphic Scoring for Sleep Laboratory Patients: Algorithm Development, Journal of Sleep Research, 2010, 19(4), p. 612-619.

Moran, F. et al., Hypoalgesia in Response to Transcutaneous Electrical Nerve Stimulation (TENS) Depends on Stimulation Intensity, The Journal of Pain, 2011, 12(8), p. 929-935.

Paquet, J. et al., Wake Detection Capacity of Actigraphy During Sleep, Sleep, 2007, 30(10), p. 1362-1369.

Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.

Sadeh, A., The Role and Validity of Actigraphy in Sleep Medicine: An Update, Sleep Medicine Reviews, 2011, vol. 15, p. 259-267.

Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.

Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.

Tryon, W. W., Issues of Validity in Actigraphic Sleep Assessment, Sleep, 2004, 27(1), p. 158-165.

Tsai, Y. et al., Impact of Subjective Sleep Quality on Glycemic Control in Type 2 Diabetes Mellitus, Family Practice, 2012, vol. 29, p. 30-35.

Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.

Webster, J. B. et al., An Activity-Based Sleep Monitor System for Ambulatory Use, Sleep, 1982, 5(4), p. 389-399.

Zelman, D. C. et al., Sleep Impairment in Patients With Painful Diabetic Peripheral Neuropathy, The Clinical Journal of Pain, 2006, 22(8), p. 681-685.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 3, p. 1039-1062.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2456.

Kovacevic-Ristanovic, R. et al., Nonpharmacologic Treatment of Periodic Leg Movements in Sleep, Arch. Phys. Med, Rehabil., 1991, vol. 72, p. 385-389.

Lopes, L. et al., Restless Legs Syndrome and Quality of Sleep in Type 2 Diabetes, Diabetes Care, 2005, vol. 28, No, 11, p. 2633-2636.

Nightingale, S., The neuropathic pain market, Nature Reviews, 2012, vol. 11, p. 101-102.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

Sheridan et al., Some Factors Influencing the Threshold of the Electrocutaneous Stimulus, Perceptual and Motor Skills, 1966, vol. 22, pp. 647-654.

\* cited by examiner

TRANSCUTANEOUS ELECTRICAL NERVE STIMULATOR WITH AUTOMATIC DETECTION OF USER SLEEP-WAKE STATE

REFERENCE TO PENDING PRIOR PATENT APPLICATIONS

This patent application:

(i) is a continuation-in-part of prior U.S. patent application Ser. No. 14/230,648, filed Mar. 31, 2014 by Shai Gozani et al. for DETECTING CUTANEOUS ELECTRODE PEELING USING ELECTRODE-SKIN IMPEDANCE; and (ii) claims benefit of prior U.S. Provisional Patent Application Ser. No. 61/811,864, filed Apr. 15, 2013 by Shai Gozani for TRANSCUTANEOUS ELECTRICAL NERVE STIMULATOR WITH AUTOMATIC DETECTION OF PATIENT SLEEP-WAKE STATE.

The two (2) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes so as to provide symptomatic relief of pain, and more particularly to detecting the sleep-wake state of the user in order to enhance the device's pain-relieving benefits at nighttime.

BACKGROUND OF THE INVENTION

Transcutaneous Electrical Nerve Stimulation (TENS) devices apply electrical currents to particular areas of the human body in order to suppress pain. The most common form of TENS is called conventional TENS. In a conventional TENS device, an electrical circuit generates stimulation current pulses with specified characteristics. The pulse waveform specifications include intensity (mA), duration (μsec) and shape (typically monophasic or biphasic). The pulse pattern specifications include the frequency (Hz) of the stimulation pulses and the length of each continuous stimulation session (minutes).

Electrical stimulation is typically delivered to the user through electrodes, with the electrical stimulation being in the form of low intensity (typically less than 100 mA), short duration (typically 50-400 μsec) pulses at frequencies typically between about 10 and 200 Hz. The electrodes are placed on the skin of the user within, adjacent to, or proximal to, the area of pain. The electrodes typically utilize hydrogels to create a stable low-impedance electrode-skin interface to facilitate the delivery of electrical current to the user so as to stimulate peripheral sensory nerves, whereby to suppress pain.

Poor sleep quality is one of the major causes of morbidity in patients suffering from chronic pain [Fishbain D A, Hall J, Meyers A L, Gonzales J, Mallinckrodt C. Does pain mediate the pain interference with sleep problem in chronic pain? Findings from studies for management of diabetic peripheral neuropathic pain with duloxetine. *J Pain Symptom Manage*. December 2008; 36(6):639-647]. It is, therefore, desirable that patients have the option of receiving TENS therapy during sleep. In fact, several studies have shown that TENS therapy can improve sleep quality (see, for example, Barbarisi M, Pace M C, Passavanti M B, et al. Pregabalin and transcutaneous electrical nerve stimulation for postherpetic neuralgia treatment. *Clin J Pain*. September 2010; 26(7):567-572).

A significant safety concern for traditional TENS use is the potential for "electrode peeling" (i.e., where the electrodes of the TENS device unintentionally separate from the skin of the user). Such electrode peeling can result in current density and power density increases due to decreased electrode-skin contact area. Increased current density and power density could lead to painful stimulation and, in the extreme, thermal burns. The U.S. Food and Drug Administration (FDA) has published draft guidelines on TENS devices that require a warning against the use of conventional TENS devices during sleep due to the risk of unintended electrode peeling [Food and Drug Administration, Draft Guidance for Industry and Staff: Class II Special Controls Guidance Document: Transcutaneous Electrical Nerve Stimulator for Pain Relief, Apr. 5, 2010]. Consequently, most TENS devices are designed to operate exclusively during the day (i.e., during wake state) without any nighttime (i.e., sleep state) operation.

In pending prior U.S. patent application Ser. No. 14/230,648, filed Mar. 31, 2014 by Shai Gozani et al. for DETECTING CUTANEOUS ELECTRODE PEELING USING ELECTRODE-SKIN IMPEDANCE, there is disclosed an invention which allows TENS therapy to be applied during nighttime (i.e., during sleep state) as well as during the day (i.e., wake state). In accordance with the aforementioned invention, the TENS device is adapted to measure electrode-skin impedance continuously during the TENS therapy for monitoring electrode-skin contact area. The known geometry of the pre-configured electrode array establishes the initial electrode-skin contact area and the analysis of subsequent electrode-skin impedance changes allows an accurate estimation of electrode-skin contact area (i.e., to detect the occurrence of electrode peeling). When the impedance reaches a critical value corresponding to a reduced contact area (i.e., the occurrence of electrode peeling) that may lead to excessive stimulation current density or power density, the device automatically terminates stimulation in order to avoid the risk of painful stimulation and, in the extreme, thermal burns.

To achieve maximum pain relief, electrical stimulation needs to be at an adequate intensity level [Moran F, Leonard T, Hawthorne S, et al. Hypoalgesia in response to transcutaneous electrical nerve stimulation (TENS) depends on stimulation intensity. *J Pain*. 12:929-935)]. The optimal TENS therapeutic intensity level is often described as the intensity level that evokes "strong but comfortable" sensation from a user. However, a stimulation intensity level tailored for daytime (i.e., wake state) use may be too strong for nighttime (i.e., sleep state) use since the stimulation intensity level appropriate for the wake state may interfere with sleep.

Another common feature of a TENS device is its "on-demand" pain relief operation. A pain-relieving TENS therapy session typically starts immediately when the user interacts with the device in a prescribed manner, such as by pressing a button on the TENS device. Each therapy session typically lasts for about 60 minutes. While on-demand therapy gives the user complete control over the timing of each TENS therapy session, on-demand therapy is not well suited for nighttime (i.e., sleep state) use as it requires deliberate and regular interaction with the TENS device by the user.

For these reasons, it would be advantageous to provide automated means to detect the user's sleep-wake state so that the TENS device can automatically alter its operation according to the daytime (i.e., wake state) or nighttime (i.e., sleep state) needs of the user. In addition to delivering effective pain therapy during the daytime, it would be advantageous if the TENS device could adjust its therapeutic stimulation parameters (such as the stimulation intensity level) during nighttime (i.e., sleep state) so as to avoid interference with sleep. Thus, in order to strengthen its utility at nighttime (i.e., during sleep state) for pain relief without interrupting sleep, the TENS device should monitor the sleep state and sleep quality of the user and adapt its operation (e.g., adjust its stimulation intensity level) accordingly.

The gold standard in determining the sleep-wake state of a subject is polysomnography which comprises at least three distinct types of data (i.e., EEG, EOG and EMG). Because of difficulty in recording and analyzing these types of data, actigraphy has been developed and refined over the last 30 years as a practical alternative to study sleep/awake patterns [Ancoli-Israel S, Cole R, Alessi C, Chambers M, Moorcroft W, Pollak C P. The role of actigraphy in the study of sleep and circadian rhythms. *Sleep*. May 1, 2003; 26(3):342-392]. Actigraphy is a continuous recording of body movement by means of a body-worn device that detects body movement, typically through the use of accelerometers. Significantly, the present invention integrates an actigraphy-based sleep-wake classification method with conventional TENS device functionality in order to provide a novel method and apparatus for enhancing the pain-relieving utility of TENS therapy at nighttime (i.e., during sleep state) without disturbing the sleep of the TENS user.

SUMMARY OF THE INVENTION

The present invention comprises the provision and use of a novel TENS device which comprises a TENS stimulator designed to be placed on the patient's upper calf (or other anatomical location) and a pre-configured electrode array designed to provide circumferential stimulation in the area of the upper calf (or other anatomical location). An accelerometer incorporated in the TENS device continuously monitors body orientation and movement of the user in order to determine the user's sleep-wake state. A key feature of the present invention is that the TENS device is adapted to adjust its stimulation parameters based on the user's sleep-wake state, which is determined by the aforementioned analysis of body orientation and movement. The user is considered to be "in-bed" if the user's body orientation is determined to be recumbent for a selected portion (e.g., a majority) of a selected time period (e.g., a decision window). A measure of user body movement, based on the concept of actigraphy, is used to quantify the user's activity level. The user is considered to be asleep if the user is "in-bed" and if the activity level (i.e., body movement) of the user remains low for a selected period of time. "In-bed" status, low activity level, and sleep state can be used individually or collectively by the TENS device to adjust stimulator output, such as stimulation pulse waveform parameters.

In one preferred form of the present invention, there is provided apparatus for transcutaneous electrical nerve stimulation in a user, the apparatus comprising:

a housing;

stimulation means for electrically stimulating at least one nerve;

an electrode releasably mounted to the housing and connectable to the stimulation means for electrical stimulation of the at least one nerve;

monitoring means for monitoring the user's body orientation and movement;

analysis means for analyzing said orientation and movement; and control means for controlling the output of the stimulation means in response to said analysis of said orientation and movement.

In another preferred form of the present invention, there is provided a method for controlling transcutaneous electrical nerve stimulation based on a user's body orientation and movement status, the method comprising the steps of:

applying the transcutaneous electrical nerve stimulation device to the user's body to create a tight mechanical coupling between the device and the user's body;

acquiring data from an accelerometer mounted to the stimulation device that measures the user's body orientation and movement;

analyzing the accelerometer data to determine the user's body orientation and movement;

determining the user's body orientation and body movement status; and modifying the stimulation output pattern based on the user's body orientation and body movement status.

In another preferred form of the present invention, there is provided apparatus for transcutaneous electrical nerve stimulation in a user, said apparatus comprising:

a housing;

stimulation means within the housing for electrically stimulating nerves;

monitoring means within the housing for measuring orientation and activity levels of the said user;

control means for controlling the electrical stimulation provided to the skin of the user when the monitoring means determines that the user body orientation and activity levels meet at least one predetermined condition.

In another preferred form of the present invention, there is provided a method for applying transcutaneous electrical nerve stimulation to a user, said method comprising:

applying stimulation means and an accelerometer sensor to the the user's body;

delivering stimulation current to the user to stimulate one or more nerves;

analyzing accelerometer sensor data to assess the user's body orientation and movement levels; and modifying the stimulation output based on the user's body orientation and movement levels.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
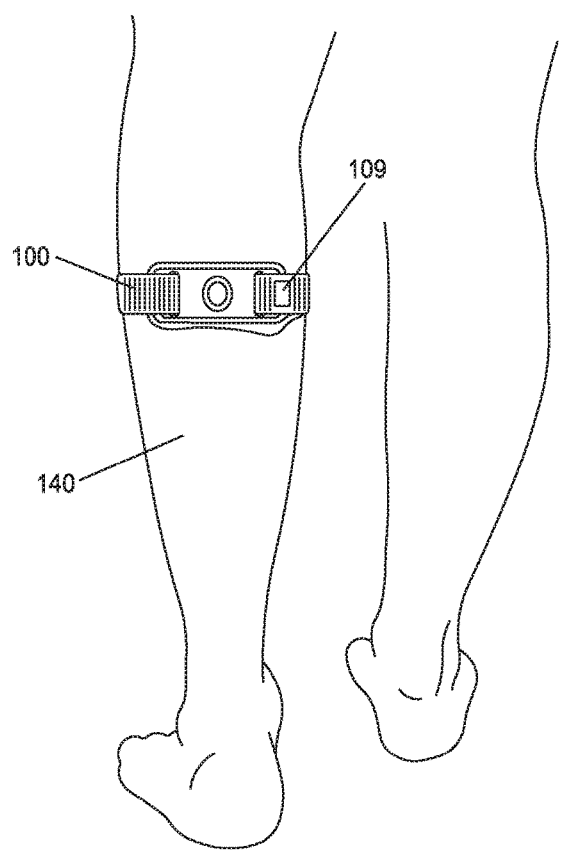
FIG. 1 is a schematic view showing a novel TENS device formed in accordance with the present invention, with the novel TENS device being mounted to the upper calf of a user.

FIG. 1 illustrates a novel TENS device 100 formed in accordance with the present invention, with the novel TENS device being shown worn on a user's upper calf 140. A user may wear one TENS device 100 on either leg, or wear two TENS devices, one on each leg.

Figure 2:
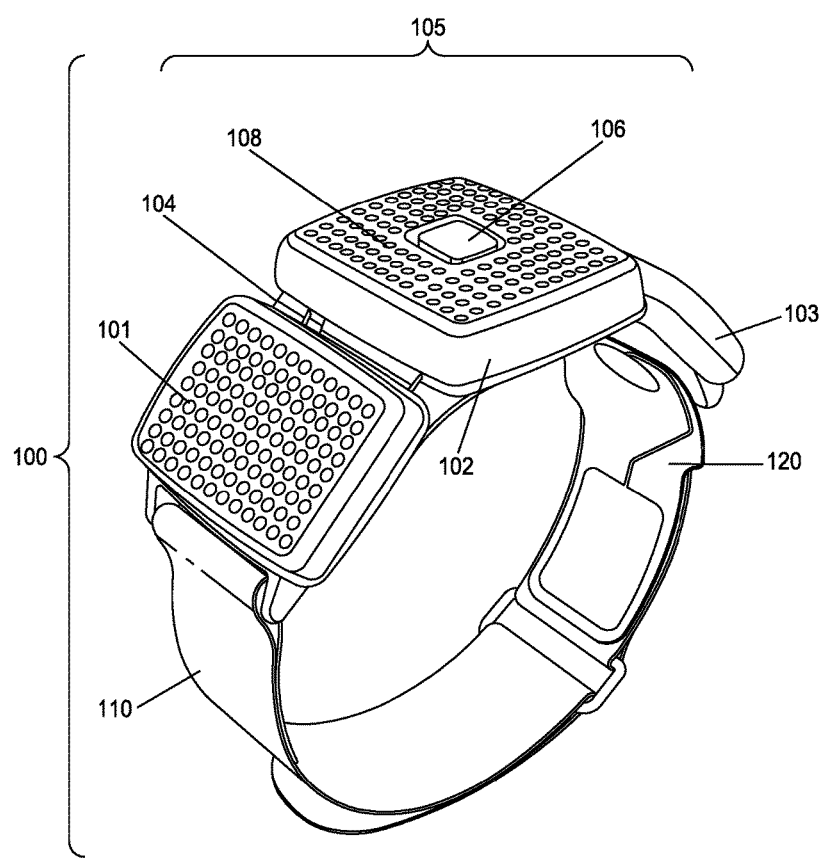
FIG. 2 is a schematic view showing the novel TENS device of FIG. 1 in greater detail.
Figure 4:
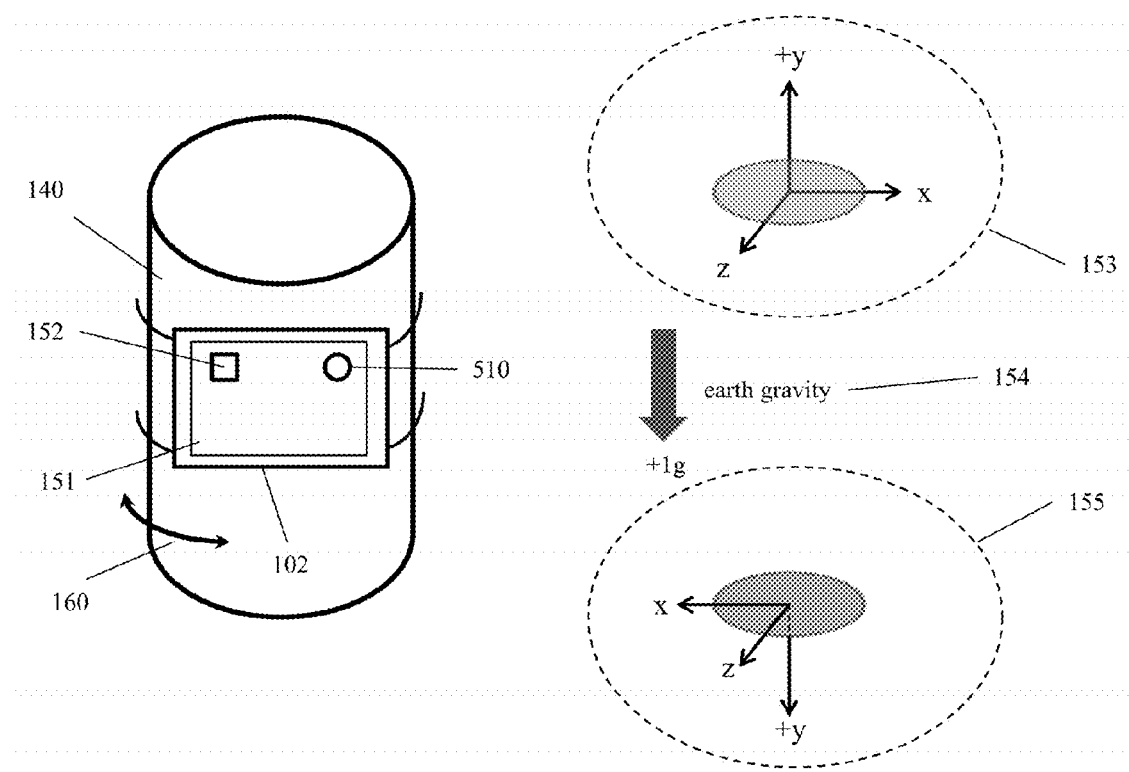
FIG. 4 is a schematic view showing the orientation of the accelerometer incorporated in the novel TENS device of FIGS. 1 and 2, when the novel TENS device of FIG. 1 is mounted to the upper calf of a user.

TENS device 100 is shown in greater detail in FIG. 2 and preferably comprises three components: a stimulator 105, a strap 110, and an electrode array 120 (comprising a cathode electrode and an anode electrode appropriately connected to stimulator 105 as is well known in the art). Stimulator 105 preferably comprises three mechanically and electrically inter-connected compartments 101, 102, and 103. Compartments 101, 102, 103 are preferably inter-connected by hinge mechanisms 104 (only one of which is shown in FIG. 2), thereby allowing TENS device 100 to conform to the curved anatomy of a user's leg. In a preferred embodiment, compartment 102 houses the TENS stimulation hardware (except for a battery) and user interface elements 106 and 108. Compartment 102 also houses an accelerometer 152 (see FIGS. 2B and 4), preferably in the form of a semiconductor chip accelerometer, for detecting user gestures, user body position and orientation, and user movement and activity levels (see below). Compartment 102 also houses a real-time clock 505 (FIG. 2B). In a preferred embodiment, compartments 101 and 103 are smaller, auxiliary compartments that house a battery for powering the TENS stimulation hardware and other ancillary elements, such as an ambient light sensor or detector 510 (FIGS. 2B and 4) for determining ambient light conditions and a wireless interface unit (not shown) for allowing TENS device 100 to wirelessly communicate with other elements (e.g., another TENS device being worn on the other leg of the user). In another embodiment of the present invention, only one compartment 102 may be provided for housing all of the TENS stimulation hardware, battery, and other ancillary elements of the present invention without the need for side compartments 101 and 103.

Still looking now at FIG. 2, interface element 106 comprises a push button for user control of electrical stimulation, and interface element 108 comprises an LED for indicating stimulation status and providing other feedback to the user. Additional user interface elements (e.g., an LCD display, audio feedback through a beeper or voice output, haptic devices such as a vibrating motor, electrical feedback by pulsing the stimulus, etc.) may also be provided and are considered to be within the scope of the present invention.

The preferred embodiment of the present invention is designed to be worn on the upper calf 140 of the user as shown in FIG. 1. TENS device 100, comprising stimulator 105, electrode array 120, and strap 110, is secured to upper calf 140 by placing the apparatus in position and then tightening strap 110. Although the preferred embodiment of the present invention comprises placement of the TENS device on the upper calf of the user, additional anatomical locations (such as above the knee, on the lower back, and on an upper extremity) are contemplated and are also considered to be within the scope of the present invention.

Figure 2A:
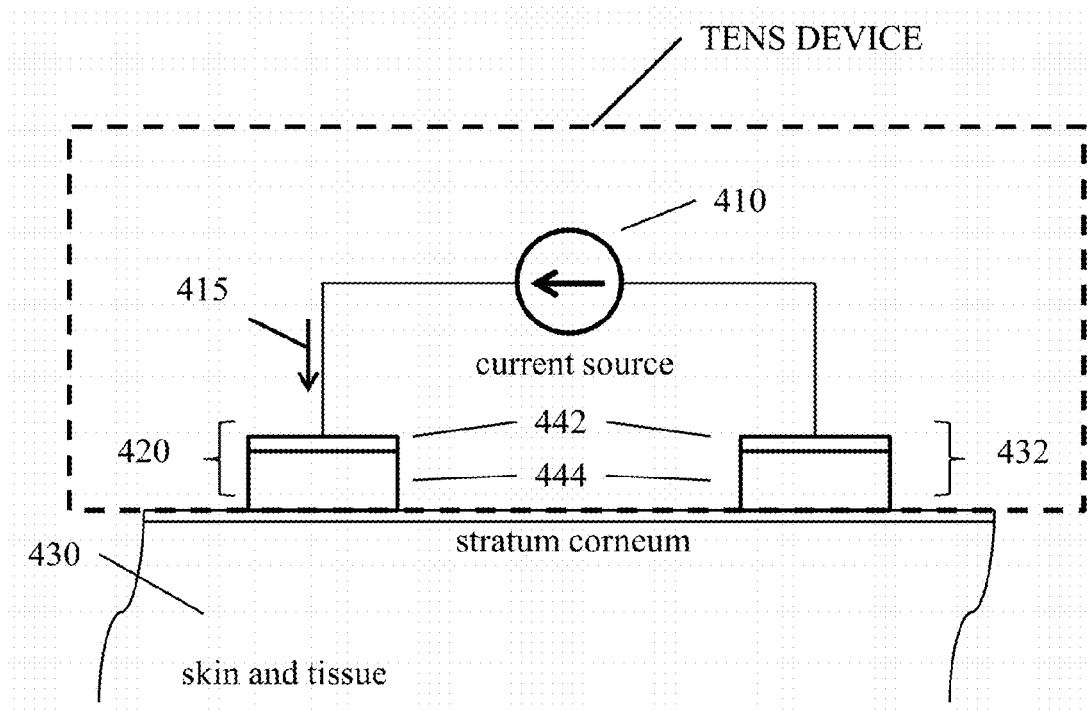
FIG. 2A is a schematic view of the novel TENS device shown in FIGS. 1 and 2.
Figure 2B:
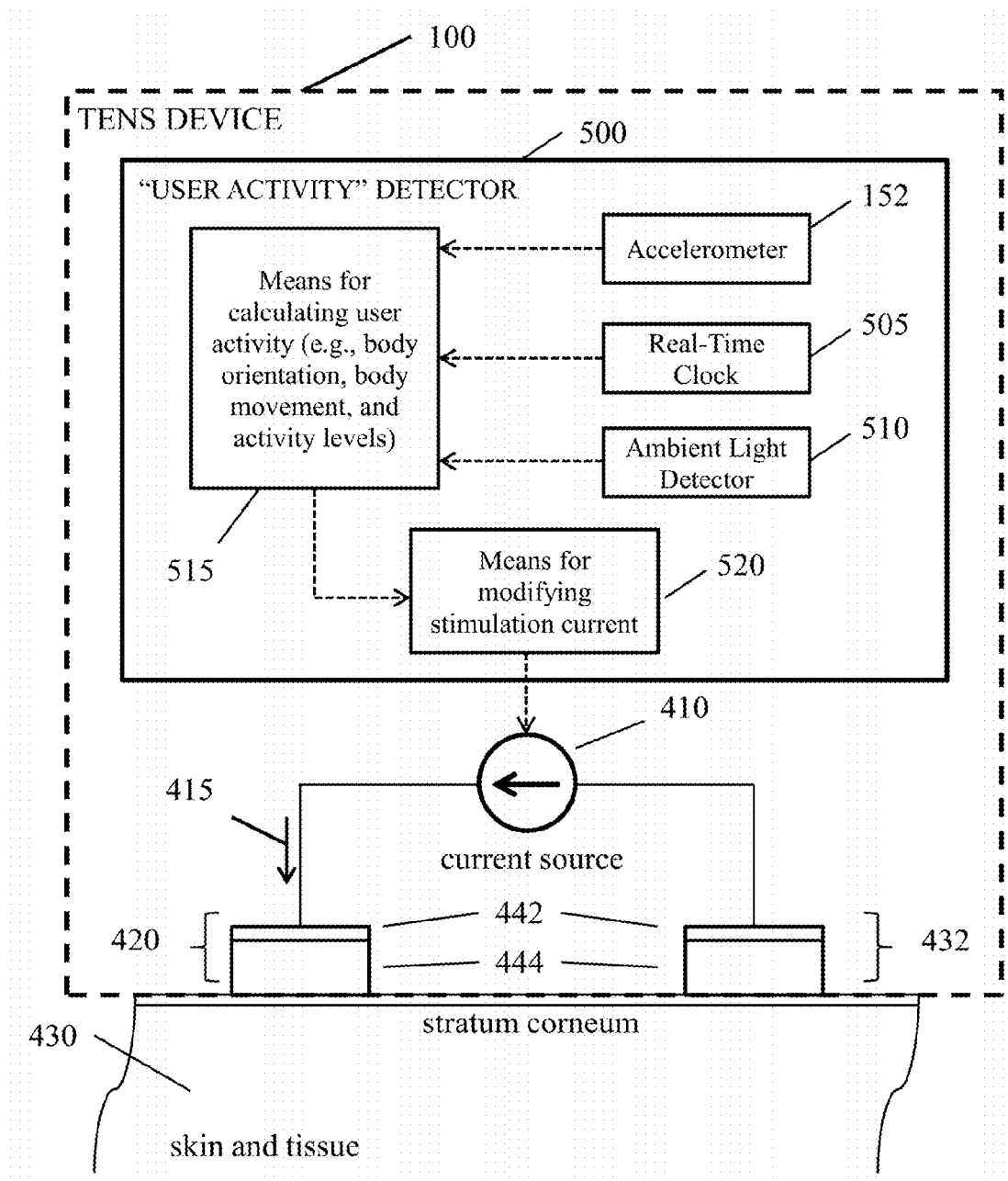
FIG. 2B is a schematic view of the novel TENS device of FIGS. 1 and 2, including its user activity detector.

FIG. 2A is a schematic representation of the current flow between a TENS device and the user. As seen in FIG. 2A, stimulation current 415 from a controlled current source 410 flows into the user's tissue 430 via cathode electrode 420. Cathode electrode 420 consists of conductive backing (e.g., silver hatch) 442 and hydrogel 444. The current passes through the user's tissue 430 and returns to current source 410 through anode electrode 432 (anode electrode 432 also comprises a conductive backing 442 and hydrogel 444). It should be appreciated that the designation of anode and cathode electrodes is purely notational in the context of a biphasic waveform (i.e., when the biphasic stimulation pulse reverses its polarity in its second phase of the biphasic TENS stimulation, current will be flowing into the user's body via interface 432 and out of the user's body via interface 420.)

Further details regarding the construction and use of the foregoing aspects of TENS device 100 are disclosed in (i) pending prior U.S. patent application Ser. No. 13/678,221, filed Nov. 15, 2012 by Shai N. Gozani et al. for APPARATUS AND METHOD FOR RELIEVING PAIN USING TRANSCUTANEOUS ELECTRICAL NERVE STIMULATION, which patent application is hereby incorporated herein by reference, and (ii) pending prior U.S. patent application Ser. No. 14/230,648, filed Mar. 31, 2014 by Shai N. Gozani et al. for DETECTING CUTANEOUS "ELECTRODE PEELING" USING ELECTRODE-SKIN IMPEDANCE, which patent application is hereby incorporated herein by reference.

When the TENS device is secured in position on the user's upper calf, the position and orientation of accelerometer 152 in TENS device 100 is fixed and known relative to the lower limb of the user. Tight mechanical coupling between TENS device 100 and lower limb 140 allows lower limb movement be accurately measured by accelerometer 152. Such tight mechanical coupling is established through strap 110. If desired, a tension gauge 109 (FIG. 1) may be provided on strap 110 to confirm that a tight mechanical coupling is established between TENS device 100 and lower limb 140. Data from accelerometer 152 are analyzed in real time to determine the orientation and movement of lower limb 140 of the user. The orientation, movement, and activity level of lower limb 140 (determined by analyzing the data from accelerometer 152) are used to determine the sleep-wake state of the user. Based on the sleep-wake state of the user, the TENS device can modify its stimulation pattern (such as the stimulation intensity level and the onset of the stimulation). A strong but comfortable stimulation intensity level may be ideal for a user during the daytime (i.e., during wake state); but the same stimulation intensity level during nighttime may evoke a sensation that prevents the user from falling asleep or may cause the user to wake up from sleep. Therefore, the TENS device is preferably configured to lower its therapeutic stimulation intensity level when the user is determined to be asleep.

The orientation and movement components measured by the present invention may contribute individually or collectively to the determination of the sleep-wake state of the user. In one preferred form of the invention, the TENS device measures calf orientation, which is highly correlated with body orientation. More particularly, upright body orientation is generally a reliable indicator that the user is in a wake state, while recumbent orientation suggests a resting state (e.g., such as occurs during sleep). Regular and robust body movement is more likely the result of user activities during the daytime (i.e., during wake state), while quiet or low-level spontaneous movements are more likely during nighttime (i.e., during sleep state). Interactions of body orientation and movement level can also be useful in identifying the sleep-wake state of the user (i.e., thereby enhancing a sleep-wake state classification). Specifically, recumbent body orientation and a low-level of physical activity is generally a good indicator that the user is asleep. In addition, real-time clock 505 allows assigning a nontrivial a priori probability of the sleep-wake state at any given time of the day in order to further refine the sleep-wake state classification results obtained by the aforementioned analysis of orientation and movement data (i.e., a user is more likely to be asleep at 3:00 am and less likely to be asleep at 4:00 pm). In a preferred embodiment of the present invention, to reflect that the a priori sleep state probability is low at a specific daytime window, the conditions for classifying user body orientation as recumbent or for classifying user sleep-wake state as asleep, can be made more stringent.

In another embodiment, output from ambient light sensor 505 is used to assign a nontrivial a priori probability of the sleep-wake state in order to improve sleep-wake classification results. In other words, ambient light sensor 505 can be used to determine if the user is in a setting which has an illuminated or non-illuminated ambience: a user is more likely to be sleeping in a dark setting than in a brightly lit setting.

FIG. 2B shows a TENS device 100 which comprises a "user activity" detector 500, wherein user activity detector 500 comprises the aforementioned accelerometer 152, real-time clock 505, ambient light detector 510, means 515 for calculating user activity (e.g., a microprocessor of the sort well known in the art, with appropriate programming to provide the functionality disclosed herein to allow a determination of user activity), and means 520 for modifying the stimulation intensity level (e.g., the magnitude of the current) according to the determination made of user activity (e.g., a controller for controlling the controlled current source 410, wherein the controller is of the sort well known in the art, controlled by the aforementioned microprocessor so as to provide the functionality disclosed herein).

On-Skin Detector

It will be appreciated that the orientation and activity measures from accelerometer 152 in TENS device 100 only become coupled with the orientation and activity of a user when the TENS device is worn by the user. In a preferred embodiment, an on-skin detector is provided to determine whether and when TENS device 100 is securely placed on the user's upper calf. Only when TENS device 100 is determined to be on-skin, does the orientation and activity data from accelerometer 152 of the TENS device become relevant in estimating the orientation and movement of the user.

Figure 3:
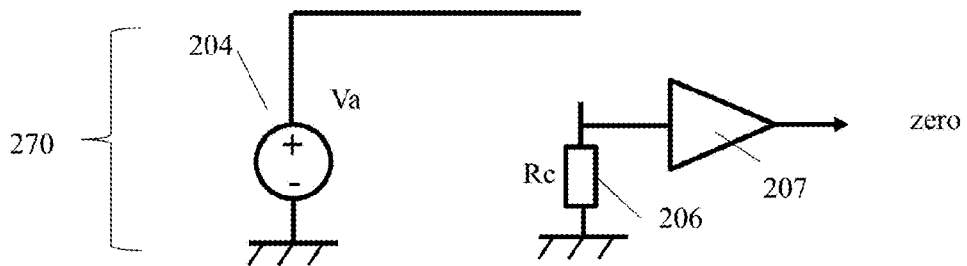
FIG. 3 is a schematic view showing the on-skin detection system of the novel TENS device shown in FIGS. 1 and 2, as well as its equivalent circuits when the novel TENS device is on and off the skin of a user.
Figure 3:
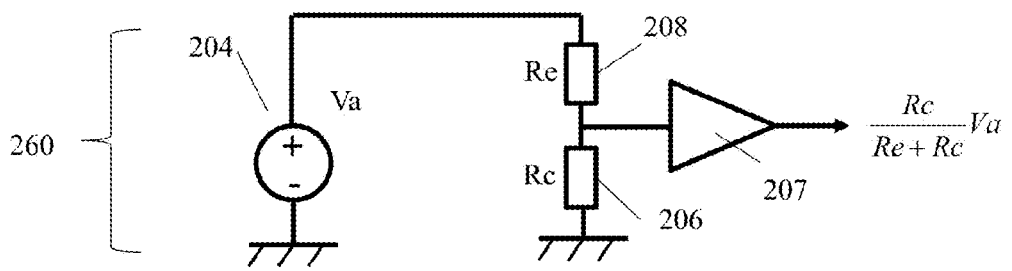
Figure 3:
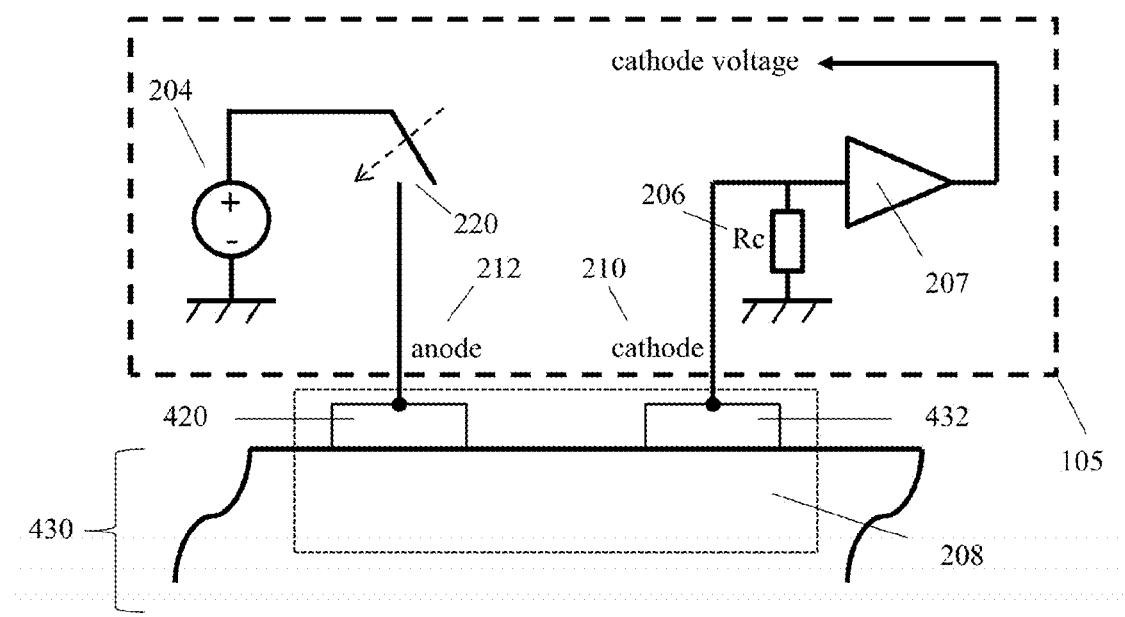

To this end, in a preferred embodiment of the present invention, and looking now at FIG. 3, the on-skin detector may be provided within TENS device 100. More particularly, in one preferred form of the invention, a voltage of 20 volts from voltage source 204 is applied to the anode terminal 212 of TENS stimulator 105 by closing the switch 220. If the TENS device is worn by the user, then user skin 430, interposed between anode electrode 420 and cathode electrode 432, will form an equivalent resistor 208 in a voltage divider circuit. More particularly, when TENS device 100 is on the skin of the user, the equivalent circuit 260 shown in FIG. 3 represents the real-world system and equivalent circuit 260 allows the anode voltage $V_a$ 204 to be sensed through the voltage divider resistors 206 and 208. The cathode voltage measured from the amplifier 207 will be non-zero and close to the anode voltage 204. On the other hand, when TENS device 100 is not on the skin of the user, the equivalent circuit 270 represents the real-world system and the cathode voltage from amplifier 207 will be zero.

Body Orientation Detection

User orientation, either upright or recumbent, may be approximated by static orientation measured by accelerometer 152 when TENS device 100 is placed on the user's upper calf 140 (FIG. 1). Strictly speaking, the accelerometer orientation matches that of the lower leg. In a preferred embodiment, and looking now at FIG. 4, accelerometer chip 152 is placed on the circuit board 151 housed inside compartment 102, so that the accelerometer's 3-axis directions 153 (i.e., x-axis, y-axis, z-axis) are known and fixed when TENS device 100 is placed on the user's upper calf.

A stationary upright user, or one sitting with feet resting on the ground, will have an upright calf orientation. Consequently, the y-axis acceleration of accelerometer 152 will have a value of about −1 g due to earth gravity 154, where g is the standard acceleration due to earth gravity. The above measurement holds true regardless of the exact rotational position 160 of compartment 102 around upper calf 140. When TENS device 100 is placed upside down on the upper calf, an allowable placement position, the accelerometer axis directions rotate as shown in 155. In this case, a stationary upright user will have a measured acceleration value along the y-axis of about +1 g. By contrast, a stationary recumbent user lying with legs flat on a bed will have a measured acceleration value along the y-axis of about 0 g. In a preferred embodiment, if the absolute value of the y-axis acceleration is greater than a threshold level, then the orientation of the user is considered to be upright, otherwise the orientation of the user is considered to be recumbent. In a preferred embodiment, this threshold level for determining upright/recumbent is 0.50 g, corresponding to a leg angle of about 30° from the horizontal plane. However, other threshold values may also be used.

Figure 5:
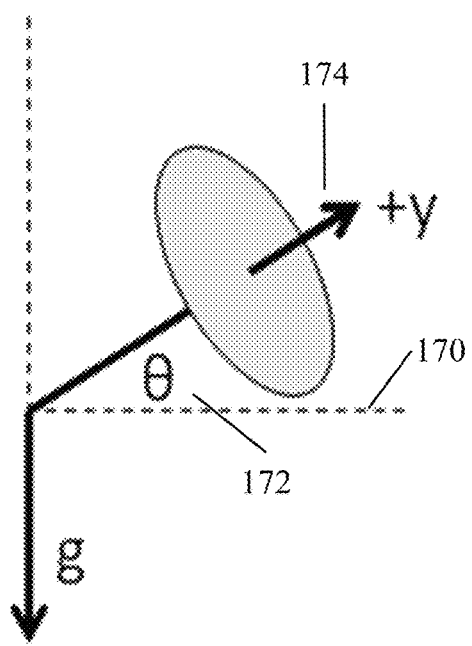
FIG. 5 is a schematic view showing the relationship between gravitational acceleration and the y-axis acceleration vector of the accelerometer in the novel TENS device when the novel TENS device (disposed on the user's leg) rests at an angle with respect to the horizontal plane.

It is unrealistic to expect a user wearing TENS device 100 to remain stationary or motionless, particularly during the daytime (i.e., during wake state). Therefore, it is advantageous to provide a method for determining body orientation that takes into account additional acceleration projected to the y-axis of accelerometer 152 due to user body movement. More particularly, and looking now at FIG. 5, where the earth's gravitational vector direction is fixed as downward, angle θ172 represents the angle between the positive accelerometer y-axis direction 174 and the true horizontal plane 170. Then the accelerometer measurement along the y-axis becomes $$A_y(t) = \pm g \sin[\theta(t)] + m(t)$$

at any given time t, where m(t) is any additional acceleration on the y-axis caused by body movement. The specific ±sign in front of g depends upon the TENS device placement on upper calf 140 and is fixed for each placement. Body movement component m(t) is considered as "noise" in the context of determining body orientation.

In a preferred embodiment, an orientation detection algorithm, taking into account user body movement, is implemented as follows.

Step 1. Set a target threshold $\theta_0$ for the angle θ so that $|\theta| < \theta_0$ corresponds to the case where the upper calf of the user is recumbent. In a preferred embodiment, the target angle threshold $\theta_0$ is set to 30°.

Step 2. Average $A_y(t)$ over a time window of length N (t=T−N+1, T−N+2, . . . , T) to reduce the effect of non-stationary noise m(t) (i.e., to reduce the effect of the body movement component m(t)). The result of this averaging is denoted as $A_{y,T}$. Estimated standard deviation $\sigma_{y,T}$ is calculated, and standard error of the mean is calculated: $SE_T = \sigma_{y,T}/\sqrt{N}$. In a preferred embodiment, the accelerometer measurements are sampled at 50 Hz and the average window length is N=3000, corresponding to a one-minute time window. Each non-overlapping window forms an "epoch". The angle $\theta_T$ is then estimated, using the formula:

$$\theta_T = \sin^{-1}[A_{y,T}]$$

where $\sin^{-1}$ is the inverse sinusoidal function.

Step 3. Calculate a context-dependent threshold $\theta_{C,T}$ that takes into account an estimation error of the angle θ and implements a hysteresis effect so as to prevent rapid switching of the body orientation state. The target threshold $\theta_0$ is adjusted by the amount $[\theta_H + \alpha^* SE_T]$ to arrive at $\theta_{C,T}$, where α relates to the confidence level of the estimated mean $A_{y,T}$. In a preferred embodiment, the hysteresis parameter $\theta_H$ is set to 2.5° and a is set to 3.0. The adjustment is by way of addition if the absolute value of the previous angle is below threshold $\theta_{C,T-1}$, such that: $\theta_{C,T} = \theta_0 + [\theta_H + \alpha^* SE_T]$; otherwise, the adjustment is by way of subtraction, such that: $\theta_{C,T} = \theta_0 - [\theta_H + \alpha^* SE_T]$.

Step 4. Compare the estimated angle $\theta_T$ (determined in Step 2) and the context-dependent threshold $\theta_{C,T}$ (determined in Step 3). If the absolute value of $\theta_T$ is greater than the context-dependent threshold $\theta_{C,T}$, then the body orientation is considered to be (i.e., the body orientation is classified as) upright for the current epoch. Otherwise, the body orientation is classified as recumbent.

Step 5. Examine the body orientation states of multiple consecutive epochs. While the body orientation of an individual epoch is accurate, the body orientation of the user over a longer time period is more informative and relevant in determining the sleep-wake state of the user. In a preferred embodiment, the majority of the body orientation over the last ten epochs is used to identify the true state of the user body orientation for the purposes of sleep-wake classification. An update to the body orientation state can be as fast as each new epoch becoming available or as slow as waiting for an entirely new set of epochs to arrive. The preferred embodiment updates body orientation state with the arrival of each new epoch. In other words, where each epoch is one minute in length, the user body orientation determination may be updated as fast as once a minute.

Thus it will be seen that user activity detector 500 of TENS device 100 uses the output of accelerometer 152 to determine the body orientation of the user. More particularly, user activity detector 500 analyzes the y-axis data received from accelerometer 152 to determine the orientation of the body of the user. In one preferred form of the invention, this is done by removing the body movement component from the y-axis data reported by accelerometer 152, and then comparing the y-axis data with the earth gravity vector g so as to determine the orientation of the body of the user.

Body Movement and Activity Levels

Human body movement is often measured quantitatively by actigraphy. Actigraphy is a continuous recording of body movement by means of a body-worn device that detects movement, typically through acceleration. Although commonly measured with a wrist-worn device, movement can be recorded at various body locations, including the lower leg. Actigraphy is effective in estimating and differentiating sleep-wake states because there is less movement during the sleep state and more movement during the wake state [Ancoli-Israel S, Cole R, Alessi C, Chambers M, Moorcroft W, Pollak C P. The role of actigraphy in the study of sleep and circadian rhythms. *Sleep*. May 1, 2003; 26(3):342-392.].

When TENS device 100 is worn on the user's upper calf 140, lower leg movement will be captured by accelerometer 152 of the TENS device. Each axis of accelerometer 152 measures the projection of the acceleration vector along that axis. Like many time-varying signals, the accelerometer measurement for each axis consists of a low frequency (slow varying) component and a high frequency (fast varying) component. The low frequency component is useful in assessing the body orientation of the user by estimating the gravitational force projection onto each axis of the accelerometer. A preferred embodiment, focusing on the y-axis measurement of the accelerometer, was described earlier for determining body orientation. The high frequency component captures acceleration as a result of user body movement events such as walking, running, climbing stairs, etc.

Although acceleration in each individual axis of the accelerometer contains unique and useful information for user body movement analysis, the instantaneous acceleration, A(t), defined in Equation 1 below, is commonly used to characterize the level of activity level, a relevant measure for sleep-wake classification.

$$A(t) = \sqrt{A_x(t)^2 + A_y(t)^2 + A_z(t)^2} \qquad \text{Eq. 1}$$

A preferred embodiment of the present invention uses the instantaneous acceleration A(t) for the actigraphy calculation. However, calculations based on other forms of acceleration combinations may also be used.

In a preferred embodiment, the single-axis acceleration components $A_x(t)$, $A_y(t)$, and $A_z(t)$ of accelerometer 152 are sampled at 50 Hz (although other sampling rates may also be used). Sampled acceleration components are band-pass filtered between 0.25 Hz and 12.0 Hz. The high-pass aspect of this band-pass filter reduces the effect of acceleration components which are not directly linked to body movement. For example, the gravitational force projection on each axis is substantially constant and its frequency is generally below 0.25 Hz, so this high-pass filter will remove that acceleration component as it is considered irrelevant to body movement activity levels. Body mass and physical limitation also constrains the frequency of accelerations caused by voluntary body movement. Filtering out frequency components higher than 12.0 Hz greatly reduces the effect of external environment factors such as high-frequency vibrations sensed by accelerometer 152 when the user is in a moving vehicle.

Filtered single-axis acceleration components $A_x(t)$, $A_y(t)$, and $A_z(t)$ are then combined via Equation 1 to form the actigraphy signal $A(t)$. In a preferred embodiment, values of $A(t)$ are averaged over one-minute epochs to yield minute-by-minute activity level counts. The T-th minute activity level count is given by Equation 2:

$$M_T = AVE_{[\text{all } t \text{ in minute } T]}\{A(t)\} \quad \text{Eq. 2}$$

In a preferred embodiment, the median of the 20 most recent activity level counts forms the "body movement measure" (BMM). Then the BMM value is compared against a pre-determined threshold value $\chi$. The user is considered to be in a low movement state if the BMM is smaller than the threshold $\chi$:

$$\text{BMM} = \text{MEDIAN}\{M_T, M_{T-1}, M_{T-2}, M_{T-19}\} < \chi \quad \text{Eq. 3}$$

Breaking the actigraphy signal $A(t)$ into one-minute epochs is a common practice in traditional actigraphy analysis for sleep study [Ancoli-Israel S, Cole R, Alessi C, Chambers M, Moorcroft W, Pollak C P. The role of actigraphy in the study of sleep and circadian rhythms. Sleep. May 1, 2003; 26(3): 342-392.]. The one-minute epoch activity level count $M_T$ also lends itself to other forms of BMM that can be easily implemented. In another embodiment, a weighted average of several epochs is used to determine BMM. The advantages of using a weighted average of several epochs to determine BMM include allowing activity level counts from more recent epochs to contribute more to the body movement measure than the counts from earlier epochs.

The movement measure threshold x may be derived from published literature or determined experimentally [Cole R J, Kripke D F, Gruen W, Mullaney D J, Gillin J C. Automatic sleep/wake identification from wrist activity. Sleep. October 1992; 15(5):461-469.] using polysomnography as a gold standard [Sadeh A. The role and validity of actigraphy in sleep medicine: an update. Sleep Med Rev. August 2011; 15(4):259-267.] [Tryon W W. Issues of validity in actigraphic sleep assessment. Sleep. Feb. 1, 2004; 27(1):158-165.]. The performance of the actigraphy signal-based BMM for sleep-wake classification is expected to have high sensitivity but low specificity for sleep [Paquet J, Kawinska A, Carrier J. Wake detection capacity of actigraphy during sleep. Sleep. October 2007; 30(10):1362-1369.]. In other words, if the user is actually sleeping, then the BMM is very likely to be low. However, if the user is in a waking but restful state then the BMM may be low as well. In a preferred embodiment, specificity is improved by using a comparatively long 20 minute monitoring window with an additional requirement of recumbent body position, which has been shown to increase specificity [Cole R J, Kripke D F, Gruen W, Mullaney D J, Gillin J C. Automatic sleep/wake identification from wrist activity. Sleep. October 1992; 15(5):461-469].

The threshold $\chi$ for BMM, however it may be initially determined, can benefit from a real-time optimization process to tailor (i.e., improve) its performance (i.e., accuracy) for individual users. For the same body movement, acceleration signals acquired by accelerometer 152 incorporated in TENS device 100 may be different in size and morphology as a result of placement variations. In addition, different users will have different body movement patterns prior to and during sleep. In one embodiment, the threshold parameter $\chi$ is initially set to a high value so that it is more sensitive for sleep classification based on BMM values. If the TENS device determines that the user is consistently awake post sleep classification, the threshold parameter $\chi$ is adjusted to a lower (i.e., more stringent) value to increase specificity. The device determination that a user is in a wake state can be based on deliberate interactions between the user and the device, an increase in BMM values in subsequent epochs, and a body orientation change to upright. Misclassification can also be determined by a significant time lag between the sleep classification event timestamp from real-time clock 505 and self-reported sleep time by the user. However, threshold parameter adjustments are preferably not based on a single misclassification but rather on a sequence of misclassifications.

The threshold $\chi$ for BMM can also be made to be a function of the user body orientation state or orientation angle. For example, when the orientation angle $\theta$ is just below the recumbent orientation threshold, the threshold $\chi$ can be made smaller to strengthen the quality of the low body movement classification. This is especially useful when the body orientation and body movement classification results are used together to determine the sleep-wake state of the user.

Thus it will be seen that user activity detector 500 of TENS device 100 uses the output of accelerometer 152 to determine the body movement and activity levels of the user. More particularly, user activity detector 500 analyzes the x, y and z-axis data received from accelerometer 152 to determine the extent of body movement of the user. In one preferred form of the invention, this is done by looking at the instantaneous acceleration of the body of the user over a period of time and comparing it against a pre-determined threshold.

Nighttime Stimulation Control

The present invention aims to maximize the pain-relieving therapeutic value of TENS device 100 while minimizing any potential interference of TENS device 100 with the sleep quality of the user when TENS therapy is delivered to the user during nighttime (i.e., sleep state). To minimize interference to sleep, operation of the TENS device should be modified before and during an actual user sleep phase, e.g., by reducing the TENS stimulation intensity level. For example, when the user is in bed and getting ready to sleep, a strong stimulation sensation may prevent the user from falling into sleep. Similarly, starting a therapy session while the user is asleep with a TENS stimulation intensity level that is appropriate for daytime use may wake the user from sleep. For the TENS device to overcome the potential disadvantages of nighttime application while remaining effective during daytime, the TENS device should modify its manner of operation in accordance with the in-bed status and the sleep-wake state of the user (i.e., the higher stimulation intensity level associated with the wake state should be reduced to a lower stimulation intensity level appropriate for the sleep state).

Body orientation and body movement can be used individually to determine whether a user is in bed or not. Combining body orientation and body movement orientation can improve the accuracy of the in-bed detection determination.

In one preferred embodiment, only body orientation is considered for the in-bed determination. When five or more epochs of the 10 most recent epochs of an observation period indicate a recumbent orientation, the user is considered to be in "in-bed" status. As a result, stimulation intensity is reduced by 2 dB (equivalent to reducing the stimulation current intensity by 20%). This lowered stimulation intensity reduces the stimulation sensation felt by the user so that the user can fall into sleep easier.

In another preferred embodiment, both orientation and BMM factors are considered. The threshold for BMM is set higher than the threshold value intended to classify the user's sleep-wake status, inasmuch as the criteria is to determine whether the user is in a "pre-sleep" in-bed state, that is, in a recumbent position with low body movement activity. In other words, a given BMM may satisfy the threshold for in-bed classification but may not satisfy the threshold for sleep classification.

It is known that an actigraphy-based sleep study often classifies a person's sleep state ahead of the reference standard based on polysomnography [Paquet J, Kawinska A, Carrier J. Wake detection capacity of actigraphy during sleep. *Sleep*. October 2007; 30(10):1362-1369.] The reason is that the recumbent position, coupled with low body movement, often precedes (but does not necessarily coincide with) the actual sleep stage. The body position and movement activity level during this "pre-sleep" in-bed period is indistinguishable from that of the actual sleep period. While this may pose a challenge for using actigraphy to classify sleep state in a traditional sleep study context, the time gap between the in-bed state and actual sleep state is advantageous for the TENS therapy application. In order to help the user to fall into sleep quickly when a TENS therapy session is ongoing, it is desirable to reduce the stimulation intensity during the "pre-sleep" phase. Otherwise, the actual sleep phase can be delayed until the current TENS therapy session is completed due to the strong sensation of the normal daytime TENS stimulation intensity.

In a preferred embodiment, the TENS therapy session will automatically restart every two hours, with each session lasting for one hour, when the TENS device determines that the in-bed status is valid. This auto-restart feature allows TENS therapy be delivered to the user throughout the night (i.e., during sleep state) so as to provide pain relief at regular intervals, such that the likelihood of the user being awoken by pain is minimized.

Thus it will be seen that user activity detector 500 of TENS device 100 uses the output of accelerometer 152 to determine the "in-bed" status of the user. More particularly, user activity detector 500 analyzes the aforementioned body orientation determination, and the aforementioned body movement and activity level determination, to determine the in-bed status of the user in order for the TENS device to modify its operation, such as reducing stimulation intensity level when the "in-bed" status is detected.

Actigraphy for Sleep Quality Monitoring

In a preferred embodiment of the present invention, body orientation and body movement are monitored during nighttime via the on-board accelerometer 152. The actigraphy-based feature BMM is used to assess sleep quality and body orientation is used so as to filter out any period during which the user may be out of bed. Activity levels during the actual TENS stimulation period are used to refine the nighttime stimulation intensity level. If the nighttime stimulation intensity level is too strong, it may cause an unconscious but deliberate reaction such as increased body movement from the user. Therefore, it is desirable for the nighttime stimulation intensity level to be adjusted where necessary in order to keep nighttime stimulation from disturbing the user (which disturbance is reflected by increased BMM).

In one preferred embodiment of the present invention, when an increase in BMM is detected during nighttime TENS stimulation, the TENS device decreases the stimulation intensity level for a pre-determined period of time (e.g., five minutes). If this decrease in the stimulation intensity level is successful in decreasing BMM (i.e., the stimulation intensity has been lowered to a level which is no longer disturbing the user), TENS device 100 is configured to "remember" the reduced stimulation intensity level for future nighttime TENS therapy sessions.

In another embodiment of the present invention, if the decrease in the stimulation intensity level is successful in decreasing BMM, the reduced stimulation intensity level is not immediately adopted for future therapy sessions. Instead, the reduced stimulation intensity level is used only when the same correlation between stimulation intensity and BMM is observed in two additional subsequent TENS therapy sessions.

When a nighttime TENS stimulation intensity is not strong enough, the TENS therapy may not effectively suppress the pain sensation, allowing the pain sensation to interfere with sleep. In this circumstance, BMM may be high due to the pain sensed by the user. In a preferred embodiment of the present invention, an increase in BMM will first trigger a decrease in the stimulation intensity level (i.e., in case the BMM is caused by excess stimulation intensity). If no noticeable decrease in BMM is thereafter observed, or the BMM continues to increase, an increase in the nighttime TENS stimulation intensity level is initiated. If the BMM decreases following the increase in the stimulation intensity level (i.e., if the increase in stimulation intensity level is effective in blocking pain and hence reducing BMM), the TENS device remembers the increased stimulation intensity level for future nighttime TENS therapy sessions.

After each TENS therapy session, the residual pain relief effect will generally continue for some period of time. The duration of this residual pain relief effect will vary from user to user. A preferred embodiment of the present invention sets a timer (not shown) incorporated in TENS device 100 for auto-restarting the next TENS therapy session one hour after completion of the previous TENS therapy session. For some users, this one hour gap between the two nighttime TENS therapy sessions may be too long to be bridged by the residual pain relief effect. Thus, in another preferred form of the invention, if the BMM increases before the auto-restart timer expires, the TENS device is configured to automatically restart the next therapy session without waiting for the auto-restart timer to expire. The preferred embodiment of the present invention preferably maintains a history of early restart instances. When the number of early restarts exceeds a pre-determined threshold, the auto-restart timer is shortened to reduce the gap between pain-relieving TENS therapy sessions.

EXAMPLE

The use of a preferred embodiment of the present invention is illustrated in the following example. The user snaps an electrode array 120 onto TENS stimulator 105 and uses strap 110 to secure TENS device 100 on upper calf 140 of the user with full electrode and skin contact (FIGS. 1 and 2). When novel TENS device 100 detects the on-skin condition (i.e., using the on-skin detector discussed above and shown in FIG. 3), the TENS device begins analyzing the accelerometer data.

Figure 6:
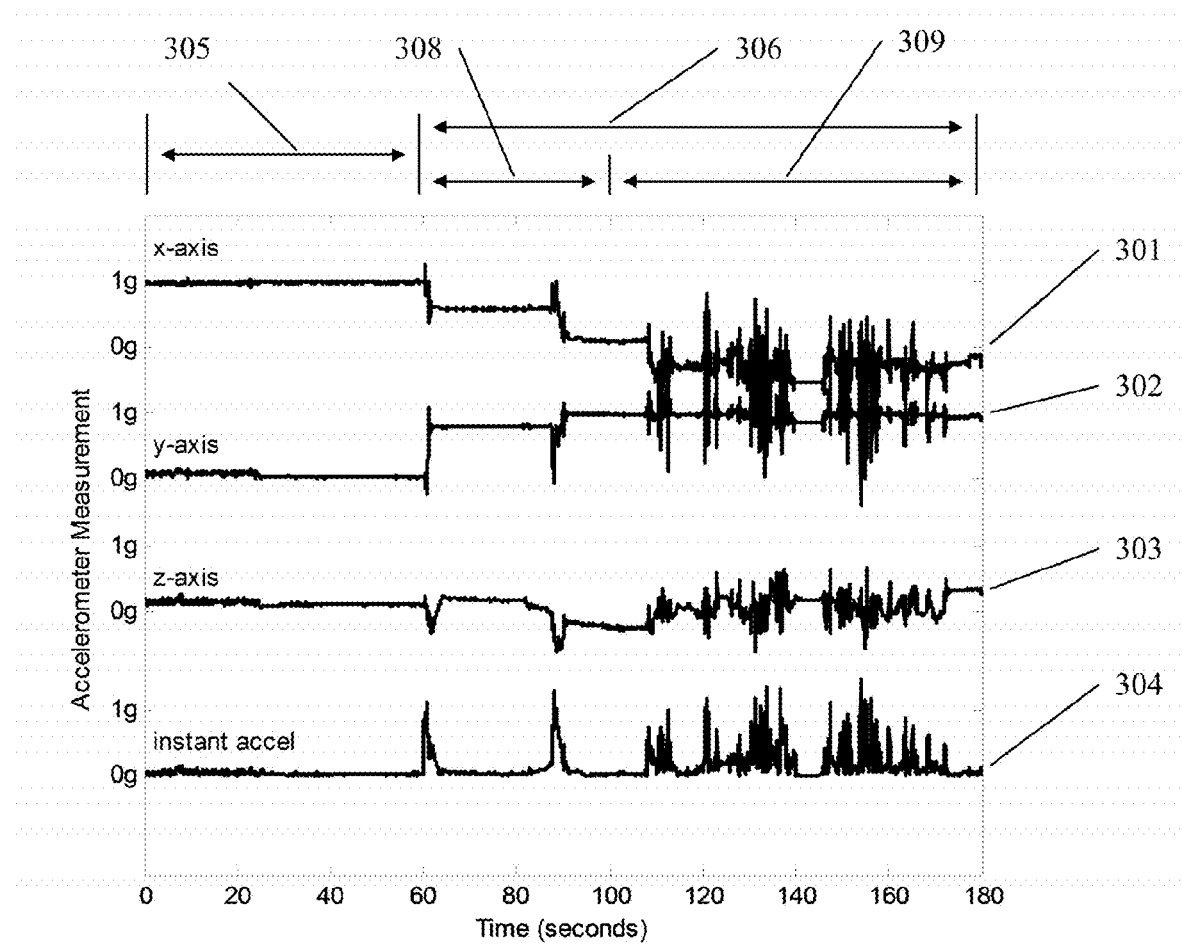
FIG. 6 is a schematic view showing the accelerometer measurements in all three axes and the calculated instantaneous acceleration values for a three-minute period with various body position and movement patterns of a user wearing the novel TENS device.

FIG. 6 shows sample traces of the data from on-board accelerometer 152 over a period of three minutes. More particularly, the top three traces shown in FIG. 6 illustrate the accelerometer output data for the x-axis direction 301, y-axis direction 302, and z-axis direction 303. The fourth trace 304 shown in FIG. 6 (i.e., the bottom trace) plots the values of the instantaneous acceleration A(t) calculated according to Equation 1 above.

Based upon the data represented by the four exemplary traces shown in FIG. 6, it can be concluded that the user's body orientation is recumbent during the first 60-second segment 305 (i.e., because zero acceleration is detected along y-axis during this time period), and it can be concluded that the user's body orientation is upright for the next 120-second segment 306 (i.e., because acceleration of 1 g is detected along the y-axis during this time period). During the next 40-second segment 308, it can be concluded that the user remains stationary, and upright, since there is little activity in the instantaneous acceleration 304 (other than orientation changes). However, during the next 80-second segment 309, it can be concluded that the user has a relatively high activity level (i.e., because there is substantial activity in the instantaneous acceleration 304). Thus, the data shown in FIG. 6 provides a basis for determining when the user is recumbent, when the user is upright, when the user is substantially stationary and when the user has a high activity level.

Figure 7:
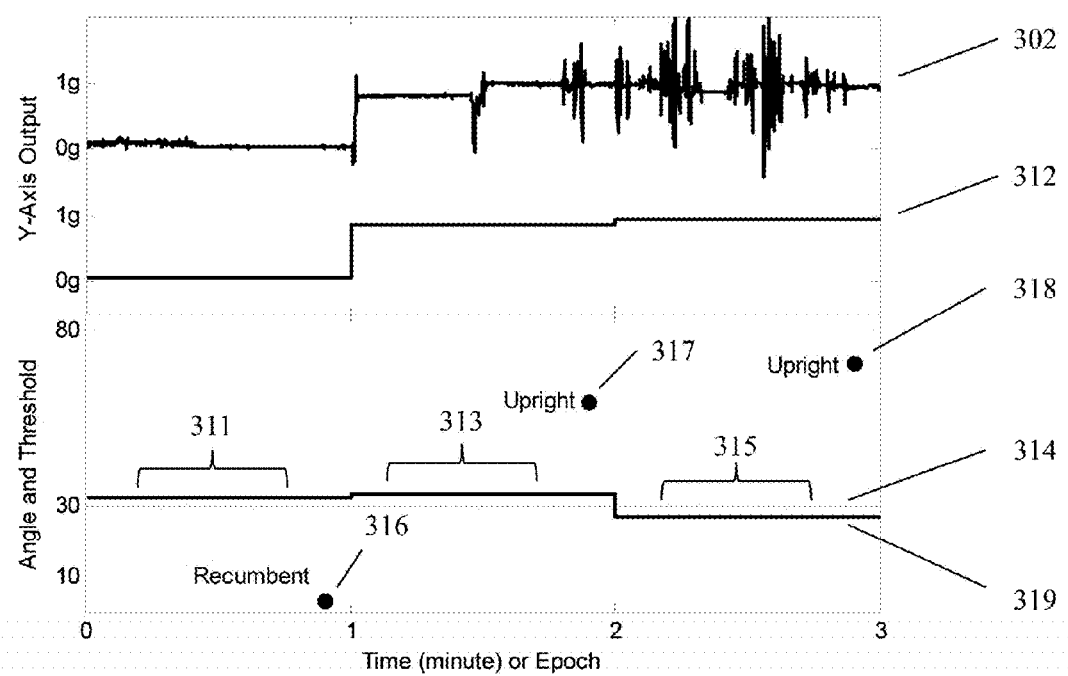
FIG. 7 is a schematic view showing the raw y-axis accelerometer measurement data, intermediate results of body orientation analysis, and the body orientation results for the same three minute period of FIG. 6.

FIG. 7 uses the same y-axis accelerometer output data to illustrate a preferred method for determining user body orientation. More particularly, and looking now at FIG. 7, when the y-axis accelerometer output 302 is to be used to determine the orientation of the user, average acceleration is first obtained for each epoch, which is defined in this example as a one-minute segment. Trace 312 shows the average acceleration value for the three epochs covered in FIGS. 6 and 7. The average acceleration values of trace 312 are mapped to the angles θ172 (FIG. 5) between the y-axis accelerometer direction 174 and the horizontal plane 170. They are compared with context-dependent angle threshold 319 (FIG. 7) in order to determine whether the body orientation is upright or recumbent. Dotted line 314 shows the targeted angle threshold of 30° in a preferred embodiment. A positive offset is added for the context-dependent angle threshold 319 for the first epoch since the prior body orientation is recumbent (not shown). The angle 316 for the first epoch is below the threshold 311 so the body orientation is classified as recumbent. Because of the recumbent orientation 316 of the first epoch, an offset is added to the target angle threshold 314 to form the context-dependent threshold 313 for the second epoch. Threshold 313 is slightly larger than threshold 311 because of the effect of an additional term in the offset: standard error of the estimated angle mean. The second epoch has larger variations in acceleration values, leading to a larger standard error and offset term. The angle of the second epoch 317 is above the threshold 313, so that the body orientation is classified as upright. Since the body orientation is classified as upright for the second epoch, the offset is subtracted from the target angle threshold 314 to form the context-dependent threshold 315 for the third epoch. Body orientation is classified as upright for the third epoch because the angle value 318 is above the context-dependent threshold 315. Thus, the data shown in FIG. 7 provides a basis for determining when the user is recumbent and when the user is upright.

Figure 8:
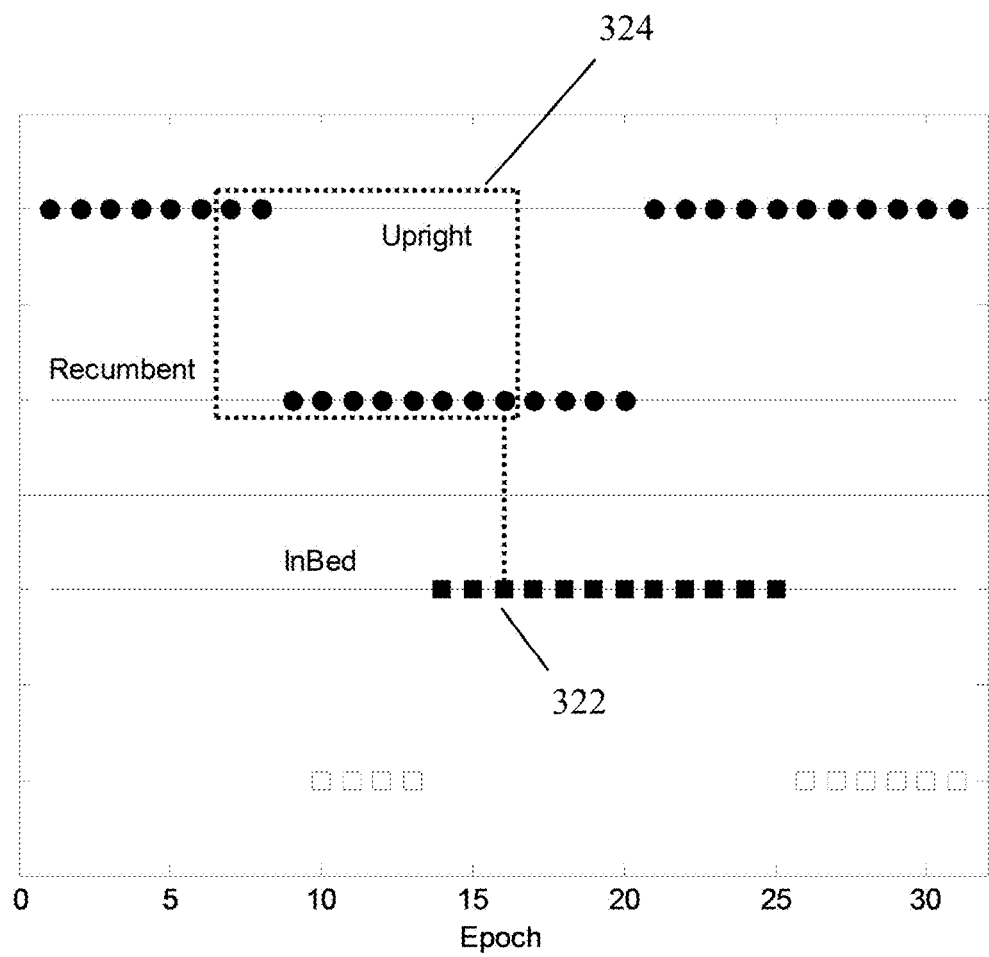
FIG. 8 is a schematic view showing body orientation results and the "in-bed" classification results based on the body orientation results of 30 epochs.

FIG. 8 shows the "in-bed" classification outcome for a sequence of upright/recumbent body orientations. A preferred embodiment of the present invention makes its epoch-by-epoch "in-bed" classification based on the 10 most recent epochs. Thus, for example, at the $16^{th}$ epoch, the "in-bed" status is considered to be "true", as indicated by a solid square 322, because 8 out of the most 10 recent body orientations (the 10 most recent body orientations for the $16^{th}$ epoch are shown within the dotted box 324) are recumbent (with only 2 of the 10 most recent body orientations being classified as upright). In the case of an even split of body orientations (e.g., 5 body orientations being classified as recumbent and 5 body orientations being classified as upright), the previous "in-bed" classification is retained for the current epoch. Thus, the data shown in FIG. 8 provides a basis for determining when the user is in-bed.

Figure 9:
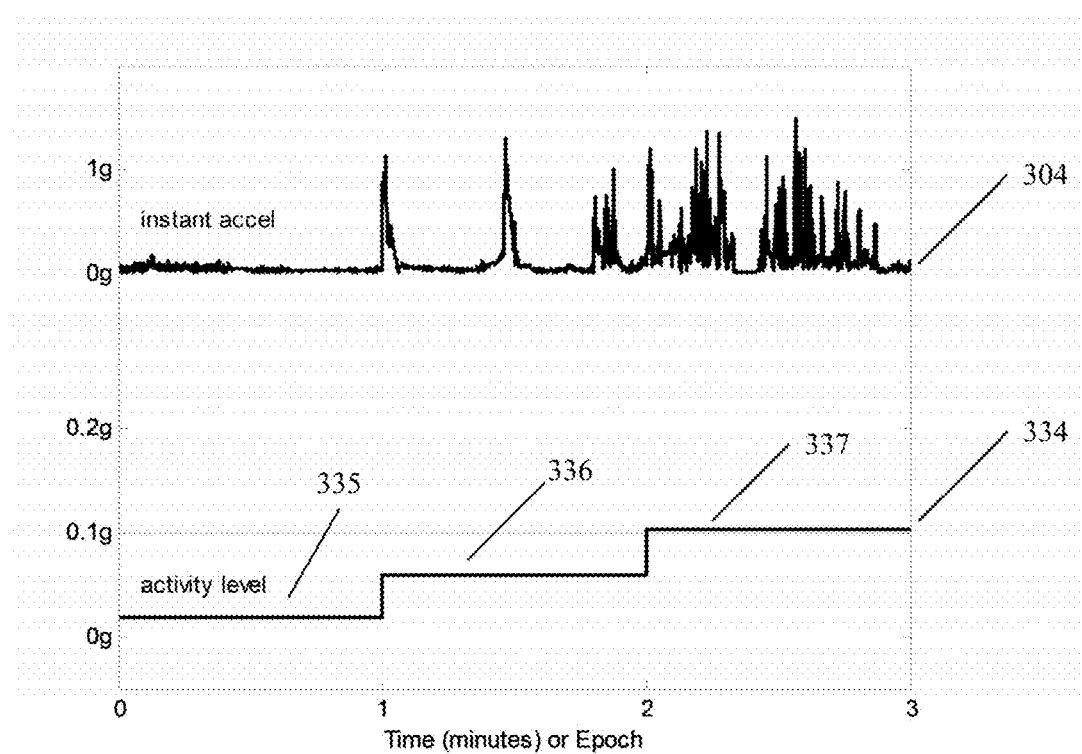
FIG. 9 is a schematic view showing the instantaneous acceleration calculated from the data shown in FIG. 6 and the corresponding activity level counts for the three-minute period of FIG. 6.

FIG. 9 illustrates the calculation results for the activity level count $M_T$. The instantaneous acceleration trace 304 from FIG. 6 is reproduced in FIG. 9. The activity level count $M_T$ for an epoch is the average of the instantaneous acceleration data within that epoch. In this example, the instantaneous acceleration data reveals that activity is progressively higher from the first epoch 335 to the second epoch 336 and to the third epoch 337. Indeed, the activity level count at the third epoch 337 is higher than that of the second epoch 336 which in turn is higher than that of the first epoch 335. The BMM for a particular time is defined as the median of the activity level counts for the most recent twenty epochs. In a preferred embodiment of the present invention, the BMM is compared against a threshold value ($\chi$) of 0.1 g. If the BMM is below the threshold value, the user's body is classified as having a "low activity" status. Thus, the data shown in FIG. 9 provides a basis for determining the user's activity level (i.e., for determining when the user should be classified as having a "low activity" status).

The preferred embodiment of the present invention uses both "in-bed" status and "low activity" status, either individually or jointly, to adjust operation of the novel TENS device. More particularly, the preferred embodiment of the present invention is configured to reduce the stimulation intensity level of TENS device 100 when the user is characterized as having "in-bed" status, or "low activity" status, or both.

Figure 10:
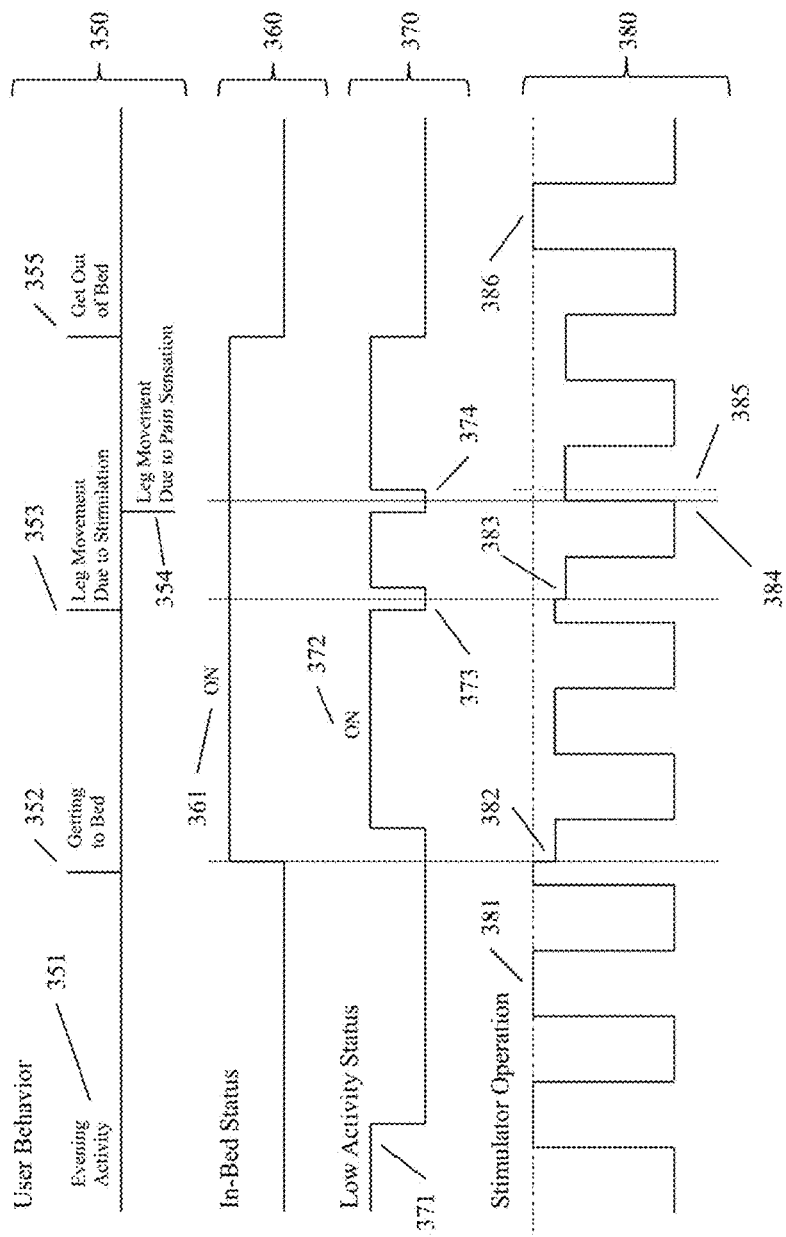
FIG. 10 is a schematic view showing the timing diagram of the interactions between the user body orientation and movement status and operation of the stimulator of the novel TENS device.

The timing diagram shown in FIG. 10 provides an example of how the novel TENS device of the present invention adjusts its stimulator operation according to the user's body and measurement status derived from the accelerometer data. FIG. 10 shows, from top to bottom, user behavior 350, user "in-bed" status 360, user "low activity" status 370, and operation of the TENS stimulator 380.

The novel TENS device is positioned on the upper calf of the user so as to trigger the on-skin condition and thereby start activity monitoring. Initially, stimulator 105 delivers normal stimulation with intensity 381 during an evening activity period 351. The "in-bed" status of the user is "off" and the "low activity" status of the user is "off" (following an initial "on" period 371).

When the user goes to bed at time 352, the data from accelerometer 152 indicates the user has become recumbent and that this body orientation has been maintained for a certain number of epochs, so the "in-bed" status is changed to the "on" state 361 (after some delay because the "in-bed" detector in the preferred embodiment requires analysis of a certain number of recumbent body position epochs in order to make the "in-bed" determination). The user may still move his/her leg for some period of time while the user is in-bed, but the user typically thereafter enters a quiet period with low BMM, so the "low activity" status is changed to the "on" state 372 after an additional delay. Nevertheless, the novel TENS device 100 reduces the intensity of its stimulator output to a lower level 382 once the "in-bed" status is turned on, in order to help the user to fall into sleep by moderating the stimulation intensity level below the "strong but comfortable" level 381 (which is more suitable for daytime TENS therapy) to the lower level 382 (which is more suitable for falling into sleep).

In the example illustrated in FIG. 10, during the night, the user is disturbed by the stimulation sensation (even at the reduced stimulation intensity level 382 discussed above) and moves his/her legs at time instance 353. This leg activity causes a change from the "low activity" status 373. The TENS stimulator 105 compensates for this by further reducing its stimulation intensity level to a new, lower stimulation intensity level 383. At time instance 354, when no TENS stimulation is being provided to the user, pain sensation causes the user to move his/her leg (while maintaining a recumbent orientation by staying in bed), so that the "low activity" status is changed to "off" at 374. The novel TENS device recognizes the combination of stimulation "off", "low activity" status "off", and "in-bed" status "on", which reflects the user experiencing pain while lying in bed. Instead of waiting until time instance 385 (when the timer would automatically start the next TENS therapy session), the TENS device automatically starts the next TENS therapy session early, (at time instance 384).

At time instance 355, the user wakes up and gets out of bed, with an upright position and an increased activity level. Both "in-bed" status and "low activity" status are turned "off" and all future TENS therapy sessions will return to the normal stimulation intensity 386 (which is appropriate for wake status use).

Thus it will be seen that, broadly speaking, the present invention uses an accelerometer incorporated in the TENS device to measure acceleration of the TENS device (and hence to measure acceleration of the body limb to which the TENS device, and hence the accelerometer, are attached) in the x-axis, y-axis and z-axis directions. The y-axis data is compared to the earth gravity vector g in the manner discussed above to determine the orientation of the user, and this orientation may be characterized as "recumbent" status or "upright" status. The x-axis data, the y-axis data and the z-axis data is used in the manner discussed above to determine body movement, and this body movement may be characterized as "low activity" status or "non-low activity" status. The recumbent/upright status and the low activity/non-low activity status is used in the manner discussed above to determine if the user is likely to be in bed, and this determination may be characterized as "in-bed" status or "non in-bed" status. The TENS device is configured so that if the user has "in-bed" status, the TENS device reduces the stimulation intensity level from a higher "wake" state level to a lower "sleep" state level. User orientation and body movement are thereafter monitored. If the user remains recumbent and body movement thereafter increases (e.g., potentially signifying that pain is awakening the user from sleep), the TENS device is configured to increase the stimulation intensity level so as to provide increased pain relief and thereby help the user remain asleep. If the user does not remain recumbent and body movement thereafter increases (e.g., potentially signifying that the user has arisen and is moving about), the TENS device is configured to increase the stimulation intensity level to a higher level (e.g., to a normal "wake" state level) so as to provide increased pain relief to the user.

Modifications of the Preferred Embodiments

Although the present invention is sometimes described above in the context of nighttime use, it should be appreciated that the activity and orientation status of the user can also be utilized during daytime use to modify the operation of the TENS stimulator. By way of example but not limitation, the activity and orientation status of the user can be used to modify the operation of the TENS stimulator during a daytime sleep session, e.g., to reduce the stimulation intensity level during a daytime nap.

Furthermore, the activity and orientation status of the user can also be used irrespective of the sleep-wake state of the user. By way of example but not limitation, the activity and orientation status of the user can be used to modify the operation of the TENS stimulator during a daytime work session (e.g., to reduce the stimulation intensity level when a user is seated at their desk), or to modify the operation of the TENS stimulator during normal daily activities (e.g., to increase the stimulation intensity level when the user is walking or running, etc.), etc.

Thus, it will be appreciated that the present invention provides a transcutaneous electrical nerve stimulator with the automatic detection of user activities, wherein the TENS stimulator may be pre-programmed to modify its operation according to the detected user activity.

Furthermore, it should be understood that many additional changes in the details, materials, steps and arrangements of parts, which have been herein described and illustrated in order to explain the nature of the present invention, may be made by those skilled in the art while still remaining within the principles and scopes of the invention.

What is claimed is:

1. Apparatus for transcutaneous electrical nerve stimulation in a user, the apparatus comprising:
   a housing;
   stimulation means for electrically stimulating at least one nerve;
   an electrode releasably mounted to the housing and connectable to the stimulation means for electrical stimulation of the at least one nerve;
   monitoring means for monitoring the user's body orientation and movement;
   analysis means for analyzing said body orientation and movement monitored by the monitoring means to determine a state of the user when the body orientation of the user is recumbent; and
   control means for automatically modifying the output of the stimulation means in response to the determination of the state of the user when the body orientation of the user is recumbent.

2. Apparatus according to claim 1 wherein the body orientation and movement are used to determine whether the user is in a sleep state or a wake state.

3. Apparatus according to claim 1 wherein the body orientation and movement are used to estimate the user's activity level.

4. Apparatus according to claim 1 wherein the body orientation and movement are used to classify the user's activity type.

5. Apparatus according to claim 1 wherein said monitoring of the user's body orientation and movement is accomplished with at least one accelerometer.

6. Apparatus according to claim 5 wherein the axis directions of the accelerometer are known and fixed with respect to a specific anatomical location of the user when a tight mechanical coupling is established between the monitoring means and the anatomical location.

7. Apparatus according to claim 6 wherein the anatomical location is the upper calf area of the user.

8. Apparatus according to claim 6 wherein the required tight mechanical coupling between the monitoring means and the anatomical location is created when a strap holds the housing, monitoring means, and electrode at the anatomical location.

9. Apparatus according to claim 8 wherein the strap includes a tension gauge to measure tightness between the monitoring means and the anatomical location.

10. Apparatus according to claim 9 wherein the tight mechanical coupling between the monitoring means and the anatomical location is confirmed through a comparison of the tension measured by the tension gauge with a tension threshold.

11. Apparatus according to claim 8 wherein the tight mechanical coupling between the monitoring means and the anatomical location is confirmed by detecting contact of said electrode with the skin of the user.

12. Apparatus according to claim 5 wherein the analysis means maps acceleration measurements from the accelerometer to the user's body orientation and body movement.

13. Apparatus according to claim 12 wherein the user's body orientation is determined by analyzing the projection value of the earth gravity acceleration vector on at least one axis of the accelerometer.

14. Apparatus according to claim 13 wherein the estimated projection value of the earth gravity acceleration vector is a function of at least one projection measurement from the accelerometer over an epoch.

15. Apparatus according to claim 14 wherein the function is an average.

16. Apparatus according to claim 14 wherein the length of an epoch is one minute.

17. Apparatus according to claim 14 wherein the projection value is expressed as an angle between said accelerometer axis and the horizontal plane.

18. Apparatus according to claim 17 wherein the absolute value of the angle is compared with a threshold in order to determine the user's body orientation as upright or recumbent.

19. Apparatus according to claim 18 wherein the user's body orientation is considered to be recumbent if the absolute value of the angle is below the threshold.

20. Apparatus according to claim 18 wherein the angle threshold has a target value and an offset.

21. Apparatus according to claim 20 wherein the target value is 30°.

22. Apparatus according to claim 20 wherein the target value is 45°.

23. Apparatus according to claim 20 wherein the target value is a function of at least one real world condition.

24. Apparatus according to claim 23 wherein the at least one real world condition comprises at least one from the group consisting of an ambient light condition, the time of the day, and a recent sleep time period pattern of the user.

25. Apparatus according to claim 20 wherein the offset has a hysteresis component to eliminate rapid orientation changes to and from the recumbent position.

26. Apparatus according to claim 25 wherein the hysteresis component is 2.5 degrees.

27. Apparatus according to claim 20 wherein the offset comprises a component which is three times the standard error of the estimated mean value of the projection.

28. Apparatus according to claim 20 wherein the offset is positive if the prior user position is recumbent.

29. Apparatus according to claim 20 wherein the offset is negative if the prior user position is upright.

30. Apparatus according to claim 12 wherein the body orientation is determined according to the majority of the body orientations of at least one most recent epochs.

31. Apparatus according to claim 12 wherein the body orientation is determined according to whether the user's body orientation remains the same for at least one most recent epoch.

32. Apparatus according to claim 1 wherein the analyzing means classifies the user state as "in-bed" if the body orientation is recumbent.

33. Apparatus according to claim 12 wherein the body movement measure is a function of at least one body activity level count derived from the acceleration measurements.

34. Apparatus according to claim 33 wherein the function is the median function.

35. Apparatus according to claim 33 wherein the function is the weighted average function.

36. Apparatus according to claim 33 wherein the number of body activity level counts is 20.

37. Apparatus according to claim 33 wherein each body activity level count is an average of an accelerometer signal over an epoch.

38. Apparatus according to claim 37 wherein an epoch is one minute in duration.

39. Apparatus according to claim 37 wherein the accelerometer signal comprises an instantaneous acceleration signal.

40. Apparatus according to claim 39 wherein the instantaneous acceleration signal is the square root of summation of squared values of filtered accelerometer measurements along each of its three axes.

41. Apparatus according to claim 40 wherein the accelerometer measurements are filtered by a band-pass filter.

42. Apparatus according to claim 1 wherein the analyzing means classify the user state as "low activity" if the user's body movement measure is below a threshold value.

43. Apparatus according to claim 42 wherein the threshold value is 0.1 g.

44. Apparatus according to claim 1 wherein the analyzing means classify the user state as sleep if the body orientation of the user is recumbent and if the user's body movement measure is below a threshold value.

45. Apparatus according to claim 1 wherein the control means modifies the stimulation means output when the user is determined to be "in-bed" or is in sleep state.

46. Apparatus according to claim 1 wherein the control means re-starts stimulation means after a timer is expired when the user is in sleep state.

47. Apparatus according to claim 46 wherein the timer defines the interval when the stimulation means is off.

48. Apparatus according to claim 47 wherein the timer duration is one hour.

49. Apparatus according to claim 47 wherein the timer duration is shortened if an increase in the user's body movement measure is observed in multiple periods during which the stimulation means are off.

50. Apparatus according to claim 1 wherein when the body orientation of the user is recumbent, the analyzing means classifies the user state as "in-bed", wherein when the user's body movement measure is below a threshold value, the analyzing means classifies the user state as "low activity", and further wherein the control means modifies the operation of the stimulation means when the "low activity" user state changes from on to off and the "in-bed" user state status is on.

51. Apparatus according to claim 50 wherein the modification to the stimulation means adjusts stimulation intensity level.

52. Apparatus according to claim 50 wherein the modification to the stimulation means adjusts stimulation pulse frequency.

53. Apparatus for transcutaneous electrical nerve stimulation in a user, said apparatus comprising:
a housing;
stimulation means within the housing for electrically stimulating nerves;
monitoring means within the housing for measuring orientation and activity levels of the user to determine a state of the user when the body orientation of the user is recumbent; and
control means for automatically modifying the electrical stimulation provided to the skin of the user in response to the determination of the state of the user when the body orientation of the user is recumbent.

54. Apparatus for providing therapeutic transcutaneous electrical nerve stimulation to a user, the apparatus comprising:
a housing;
stimulation means for electrically stimulating at least one nerve;
monitoring means for monitoring the user's body orientation and movement;
analysis means for analyzing said body orientation and movement monitored by the monitoring means to determine whether the user is in a sleep state or a wake state; and
control means for automatically modifying the output of the stimulation means in response to the determination of the sleep-wake state of the user so that therapeutic stimulation is delivered to the user in a sleep state.

55. Apparatus according to claim 54 wherein the control means modifies the output of the stimulation means so that a first therapeutic stimulation intensity level is delivered to the at least one nerve of the user when the user is determined to be in a wake state and a second therapeutic stimulation, with an intensity level lower than the first therapeutic stimulation intensity, is delivered to the at least one nerve of the user when the user is determined to be in a sleep state.

56. Apparatus according to claim 54 wherein the control means modifies the output of the stimulation means so that a first therapeutic stimulation intensity level is delivered to the at least one nerve of the user when the user is determined to be in a sleep state and a second therapeutic stimulation, with an intensity level higher than the first therapeutic stimulation intensity, is delivered to the at least one nerve of the user when the user is determined to be likely to transition to a wake state.

* * * * *